(12) United States Patent
Bergmann et al.

(10) Patent No.: US 11,739,378 B2
(45) Date of Patent: *Aug. 29, 2023

(54) POLYPEPTIDE TAGGED NUCLEOTIDES AND USE THEREOF IN NUCLEIC ACID SEQUENCING BY NANOPORE DETECTION

(71) Applicants: Roche Molecular Systems, Inc., Pleasanton, CA (US); Roche Sequencing Solutions, Inc., Pleasanton, CA (US)

(72) Inventors: Frank Bergmann, Iffeldorf (DE); Christoph Seidel, Weilheim (DE); Andrew Trans, Mountain View, CA (US); Dmitriy Gremyachinskiy, Sunnyvale, CA (US); Hannes Kuchelmeister, Munich (DE); Lars Hillringhaus, Konigsdorf-Schonrain (DE)

(73) Assignees: Roche Sequencing Solutions, Inc., Pleasanton, CA (US); Roche Molecular Systems, Inc., Pleasanton, CA (US)

( * ) Notice: Subject to any disclaimer, the term of this patent is extended or adjusted under 35 U.S.C. 154(b) by 106 days.

This patent is subject to a terminal disclaimer.

(21) Appl. No.: 17/201,834

(22) Filed: Mar. 15, 2021

(65) Prior Publication Data
US 2022/0090189 A1    Mar. 24, 2022

Related U.S. Application Data

(63) Continuation of application No. 15/770,922, filed as application No. PCT/EP2016/070198 on Aug. 26, 2016, now Pat. No. 10,975,426.

(60) Provisional application No. 62/216,634, filed on Sep. 10, 2015.

(51) Int. Cl.
| | | |
|---|---|---|
| *C12Q 1/68* | (2018.01) | |
| *C07H 19/10* | (2006.01) | |
| *C07H 19/20* | (2006.01) | |
| *C12Q 1/6869* | (2018.01) | |

(52) U.S. Cl.
CPC .......... *C12Q 1/6869* (2013.01); *C07H 19/10* (2013.01); *C07H 19/20* (2013.01); *C12Q 2525/113* (2013.01); *C12Q 2525/197* (2013.01); *C12Q 2525/203* (2013.01); *C12Q 2525/204* (2013.01); *C12Q 2565/631* (2013.01)

(58) Field of Classification Search
CPC ........ C12Q 1/6869; C07H 19/10; C07H 19/20
See application file for complete search history.

(56) References Cited

U.S. PATENT DOCUMENTS

| | | | |
|---|---|---|---|
| 8,652,779 B2 | 2/2014 | Turner | |
| 10,975,426 B2* | 4/2021 | Bergmann | ............. C07H 19/10 |
| 2013/0244340 A1 | 9/2013 | Davis | |
| 2013/0264207 A1 | 10/2013 | Ju | |
| 2014/0134616 A1 | 5/2014 | Davis | |
| 2014/0309144 A1 | 10/2014 | Turner | |

FOREIGN PATENT DOCUMENTS

| | | |
|---|---|---|
| WO | 2005024380 A2 | 3/2005 |
| WO | 2013154999 A2 | 10/2013 |
| WO | 2013191793 A1 | 12/2013 |

OTHER PUBLICATIONS

Gibson, Bradford W., et al., "Mass spectrometric characterization of a series of adenosylated peptides acting as bisubstrate analogs of protein kinases", Journal of the American Society for Mass Spectrometry, US, (May 1, 1994), vol. 5, No. 5, doi:10.1016/1044-0305(94)85060-7, ISSN 1044-0305, pp. 443-451, XP055313933.
Kumar, et al., "PEG-Labeled Nucleotides and Nanopore Detection for Single Molecule DNA Sequencing by Synthesis", Scientific Reports, 2012, 2:684; DOI: 10.1038/srep00684.
Piecyk, K ., et al., Chemical conjugation of an mRNA cap analogue with a cell-penetrating peptide as a potential Membrane permeable translation inhibitor, Tetrahedron Letters, (2014), pp. 606-609, 55, Elsevier Ltd.
Stefureac, et al., Modulation of the translocation of peptides through nanopores by the application of an AC electric field, Chem. Commun., Dec. 7, 2011, vol. 48.
Stefureac, et al., "Transport of alpha-helical peptides through alpha-hemolysin and aerolysin pores", Biochemistry. Aug. 1, 2006;45(30):9172-9.

* cited by examiner

*Primary Examiner* — Jezia Riley
(74) *Attorney, Agent, or Firm* — FisherBroyles, LLP; Adam K. Whiting; Jason M. Pass

(57) ABSTRACT

The present disclosure relates to compositions and methods based on polypeptide-tagged nucleotide, and the use of such polypeptide-tagged nucleotides in nanopore devices and methods.

16 Claims, 3 Drawing Sheets
Specification includes a Sequence Listing.

SEQUENCE LISTING

<160> NUMBER OF SEQ ID NOS: 24

<210> SEQ ID NO 1
<211> LENGTH: 69
<212> TYPE: PRT
<213> ORGANISM: Artificial Sequence
<220> FEATURE:
<223> OTHER INFORMATION: Synthetic peptide

<400> SEQUENCE: 1

Glu Ala Ala Ala Glu Ala Ala Ala Glu Ala Ala Ala Glu Ala Ala Ala
1               5                   10                  15

Glu Ala Ala Ala Glu Ala Ala Ala Glu Ala Ala Ala Glu Ala Ala Ala
            20                  25                  30

Glu Ala Ala Ala Glu Ala Ala Ala Glu Ala Ala Ala Glu Ala Ala Ala
        35                  40                  45

Glu Ala Ala Ala Glu Ala Ala Ala Glu Ala Ala Ala Glu Ala Ala Ala
    50                  55                  60

Glu Glu Glu Glu Glu
65

<210> SEQ ID NO 2
<211> LENGTH: 57
<212> TYPE: PRT
<213> ORGANISM: Artificial Sequence
<220> FEATURE:
<223> OTHER INFORMATION: Synthetic peptide

<400> SEQUENCE: 2

Glu Ala Ala Ala Glu Ala Ala Ala Glu Ala Ala Ala Glu Ala Ala Ala
1               5                   10                  15

Glu Ala Ala Ala Glu Ala Ala Ala Glu Ala Ala Ala Glu Ala Ala Ala
            20                  25                  30

Glu Ala Ala Ala Glu Ala Ala Ala Glu Ala Ala Ala Glu Ala Ala Ala
        35                  40                  45

Glu Ala Ala Ala Glu Glu Glu Glu Glu
    50                  55

<210> SEQ ID NO 3
<211> LENGTH: 45
<212> TYPE: PRT
<213> ORGANISM: Artificial Sequence
<220> FEATURE:
<223> OTHER INFORMATION: synthetic peptide

<400> SEQUENCE: 3

```
Glu Ala Ala Ala Glu Ala Ala Ala Glu Ala Ala Ala Glu Ala Ala Ala
1               5                   10                  15

Glu Ala Ala Ala Glu Ala Ala Ala Glu Ala Ala Ala Glu Ala Ala Ala
            20                  25                  30

Glu Ala Ala Ala Glu Ala Ala Ala Glu Glu Glu Glu Glu
        35                  40                  45
```

<210> SEQ ID NO 4
<211> LENGTH: 69
<212> TYPE: PRT
<213> ORGANISM: Artificial Sequence
<220> FEATURE:
<223> OTHER INFORMATION: synthetic peptide

<400> SEQUENCE: 4

```
Glu Ala Ala Ala Glu Ala Ala Ala Glu Ala Ala Ala Glu Ala Ala Ala
1               5                   10                  15

Glu Ala Ala Ala Glu Ala Ala Ala Glu Ala Ala Ala Glu Ala Ala Ala
            20                  25                  30

Glu Ala Ala Ala Glu Ala Ala Ala Glu Ala Ala Ala Glu Ala Ala Ala
        35                  40                  45

Glu Ala Ala Ala Glu Ala Ala Ala Glu Ala Ala Ala Glu Ala Ala Ala
    50                  55                  60

Gly Gly Gly Gly Glu
65
```

<210> SEQ ID NO 5
<211> LENGTH: 50
<212> TYPE: PRT
<213> ORGANISM: Artificial Sequence
<220> FEATURE:
<223> OTHER INFORMATION: synthetic peptide

<400> SEQUENCE: 5

```
Ala Glu Ala Glu Ala Glu Ala Glu Ala Glu Ala Glu Ala Glu Ala Glu
1               5                   10                  15

Ala Glu Ala Glu Ala Glu Ala Glu Ala Glu Ala Glu Ala Glu Ala Glu
            20                  25                  30

Ala Glu Ala Glu Ala Glu Ala Glu Ala Glu Ala Glu Ala Glu Ala Glu
        35                  40                  45

Ala Glu
    50
```

<210> SEQ ID NO 6
<211> LENGTH: 70
<212> TYPE: PRT
<213> ORGANISM: Artificial Sequence
<220> FEATURE:
<223> OTHER INFORMATION: synthetic peptide

<400> SEQUENCE: 6

Glu Ala Ala Glu Ala Ala Glu Ala Ala Glu Ala Ala
1               5                   10                  15

Glu Ala Ala Glu Ala Ala Glu Ala Ala Glu Ala Ala
        20                  25                  30

Pro Glu Ala Ala Glu Ala Ala Glu Ala Ala Glu Ala Ala
            35                  40                  45

Ala Glu Ala Ala Ala Glu Ala Ala Glu Ala Ala Glu Ala Ala
    50                  55                  60

Ala Glu Glu Glu Glu Glu
65              70

<210> SEQ ID NO 7
<211> LENGTH: 72
<212> TYPE: PRT
<213> ORGANISM: Artificial Sequence
<220> FEATURE:
<223> OTHER INFORMATION: synthetic peptide

<400> SEQUENCE: 7

Glu Ala Ala Ala Glu Ala Ala Ala Glu Ala Ala Ala Glu Ala Ala
1               5                   10                  15

Pro Glu Ala Ala Ala Glu Ala Ala Ala Glu Ala Ala Ala Glu Ala Ala
            20                  25                  30

Ala Pro Glu Ala Ala Ala Glu Ala Ala Ala Glu Ala Ala Ala Glu Ala
            35                  40                  45

Ala Ala Pro Glu Ala Ala Ala Glu Ala Ala Ala Glu Ala Ala Ala Glu
        50                  55                  60

Ala Ala Ala Glu Glu Glu Glu Glu
65              70

<210> SEQ ID NO 8
<211> LENGTH: 69
<212> TYPE: PRT
<213> ORGANISM: Artificial Sequence
<220> FEATURE:
<223> OTHER INFORMATION: synthetic peptide

<400> SEQUENCE: 8

Glu Ala Ala Ala Lys Ala Ala Ala Glu Ala Ala Ala Lys Ala Ala Ala
1               5                   10                  15

Glu Ala Ala Ala Lys Ala Ala Ala Glu Ala Ala Ala Lys Ala Ala Ala
            20                  25                  30

Glu Ala Ala Ala Glu Ala Ala Ala Glu Ala Ala Ala Glu Ala Ala Ala
            35                  40                  45

Glu Ala Ala Ala Glu Ala Ala Ala Glu Ala Ala Ala Glu Ala Ala Ala
        50                  55                  60

Glu Glu Glu Glu Glu
65

<210> SEQ ID NO 9
<211> LENGTH: 69
<212> TYPE: PRT
<213> ORGANISM: Artificial Sequence
<220> FEATURE:
<223> OTHER INFORMATION: synthetic peptide

```
<400> SEQUENCE: 9

Glu Ala Ala Ala Lys Ala Ala Glu Ala Ala Ala Lys Ala Ala Ala
1               5                   10                  15

Glu Ala Ala Ala Lys Ala Ala Glu Ala Ala Ala Lys Ala Ala Ala
                20                  25                  30

Glu Ala Ala Ala Lys Ala Ala Glu Ala Ala Ala Lys Ala Ala Ala
            35                  40                  45

Glu Ala Ala Ala Lys Ala Ala Glu Ala Ala Ala Lys Ala Ala Ala
        50                  55                  60

Glu Glu Glu Glu Glu
65

<210> SEQ ID NO 10
<211> LENGTH: 55
<212> TYPE: PRT
<213> ORGANISM: Artificial Sequence
<220> FEATURE:
<223> OTHER INFORMATION: synthetic peptide

<400> SEQUENCE: 10

Glu Pro Pro Pro Pro Pro Pro Pro Glu Pro Pro Pro Pro Pro Pro
1               5                   10                  15

Pro Pro Pro Glu Pro Pro Pro Pro Pro Pro Pro Pro Pro Glu Pro
                20                  25                  30

Pro Pro Pro Pro Pro Pro Pro Glu Pro Pro Pro Pro Pro Pro Pro
            35                  40                  45

Pro Pro Glu Glu Glu Glu Glu
        50                  55

<210> SEQ ID NO 11
<211> LENGTH: 69
<212> TYPE: PRT
<213> ORGANISM: Artificial Sequence
<220> FEATURE:
<223> OTHER INFORMATION: synthetic peptide

<400> SEQUENCE: 11

Glu Pro Pro Pro Glu Pro Pro Glu Pro Pro Glu Pro Pro Pro Pro
1               5                   10                  15

Glu Pro Pro Pro Glu Pro Pro Pro Glu Pro Pro Glu Pro Pro Pro
                20                  25                  30

Glu Pro Pro Pro Glu Pro Pro Pro Glu Pro Pro Glu Pro Pro Pro
            35                  40                  45

Glu Pro Pro Pro Glu Pro Pro Pro Glu Pro Pro Glu Pro Pro Pro
        50                  55                  60

Glu Glu Glu Glu Glu
65

<210> SEQ ID NO 12
<211> LENGTH: 50
<212> TYPE: PRT
<213> ORGANISM: Artificial Sequence
<220> FEATURE:
<223> OTHER INFORMATION: synthetic peptide

<400> SEQUENCE: 12

Pro Pro Pro Pro Pro Pro Pro Pro Pro Pro Pro Pro Pro Pro Pro
1               5                   10                  15

Pro Pro Pro Pro Pro Pro Pro Pro Pro Pro Pro Pro Pro Pro Pro
                20                  25                  30
```

```
Pro Pro Pro Pro Pro Pro Pro Pro Pro Pro Pro Pro Glu Glu Glu
        35                  40                  45

Glu Glu
    50

<210> SEQ ID NO 13
<211> LENGTH: 69
<212> TYPE: PRT
<213> ORGANISM: Artificial Sequence
<220> FEATURE:
<223> OTHER INFORMATION: synthetic peptide

<400> SEQUENCE: 13

Arg Ala Ala Ala Arg Ala Ala Ala Arg Ala Ala Ala Arg Ala Ala Ala
1               5                   10                  15

Arg Ala Ala Ala Arg Ala Ala Ala Arg Ala Ala Ala Arg Ala Ala Ala
            20                  25                  30

Arg Ala Ala Ala Arg Ala Ala Ala Arg Ala Ala Ala Arg Ala Ala Ala
        35                  40                  45

Arg Ala Ala Ala Arg Ala Ala Ala Arg Ala Ala Ala Arg Ala Ala Ala
    50                  55                  60

Arg Arg Arg Arg Arg
65

<210> SEQ ID NO 14
<211> LENGTH: 69
<212> TYPE: PRT
<213> ORGANISM: Artificial Sequence
<220> FEATURE:
<223> OTHER INFORMATION: synthetic peptide

<400> SEQUENCE: 14

Glu Ala Thr Ala Glu Ala Thr Ala Glu Ala Thr Ala Glu Ala Thr Ala
1               5                   10                  15

Glu Ala Thr Ala Glu Ala Thr Ala Glu Ala Thr Ala Glu Ala Thr Ala
            20                  25                  30

Glu Ala Thr Ala Glu Ala Thr Ala Glu Ala Thr Ala Glu Ala Thr Ala
        35                  40                  45

Glu Ala Thr Ala Glu Ala Thr Ala Glu Ala Thr Ala Glu Ala Thr Ala
    50                  55                  60

Glu Glu Glu Glu Glu
65

<210> SEQ ID NO 15
<211> LENGTH: 70
<212> TYPE: PRT
<213> ORGANISM: Artificial Sequence
<220> FEATURE:
<223> OTHER INFORMATION: synthetic peptide

<400> SEQUENCE: 15

Gly Glu Ala Ala Ala Glu Ala Ala Ala Glu Ala Ala Ala Glu Ala Ala
1               5                   10                  15

Ala Glu Ala Ala Ala Glu Ala Ala Ala Glu Ala Ala Ala Glu Ala Ala
            20                  25                  30

Ala Glu Ala Ala Ala Glu Ala Ala Ala Glu Ala Ala Ala Glu Ala Ala
        35                  40                  45
```

Ala Glu Ala Ala Ala Glu Ala Ala Ala Glu Ala Ala
    50                  55                  60

Ala Glu Glu Glu Glu Glu
65                  70

<210> SEQ ID NO 16
<211> LENGTH: 58
<212> TYPE: PRT
<213> ORGANISM: Artificial Sequence
<220> FEATURE:
<223> OTHER INFORMATION: synthetic peptide

<400> SEQUENCE: 16

Gly Glu Ala Ala Ala Glu Ala Ala Ala Glu Ala Ala Ala Glu Ala Ala
1               5                   10                  15

Ala Glu Ala Ala Ala Glu Ala Ala Ala Glu Ala Ala Ala Glu Ala Ala
                20                  25                  30

Ala Glu Ala Ala Ala Glu Ala Ala Ala Glu Ala Ala Ala Glu Ala Ala
            35                  40                  45

Ala Glu Ala Ala Ala Glu Glu Glu Glu Glu
        50                  55

<210> SEQ ID NO 17
<211> LENGTH: 46
<212> TYPE: PRT
<213> ORGANISM: Artificial Sequence
<220> FEATURE:
<223> OTHER INFORMATION: synthetic peptide

<400> SEQUENCE: 17

Gly Glu Ala Ala Ala Glu Ala Ala Ala Glu Ala Ala Ala Glu Ala Ala
1               5                   10                  15

Ala Glu Ala Ala Ala Glu Ala Ala Ala Glu Ala Ala Ala Glu Ala Ala
                20                  25                  30

Ala Glu Ala Ala Ala Glu Ala Ala Ala Glu Glu Glu Glu Glu
            35                  40                  45

<210> SEQ ID NO 18
<211> LENGTH: 71
<212> TYPE: PRT
<213> ORGANISM: Artificial Sequence
<220> FEATURE:
<223> OTHER INFORMATION: synthetic peptide

<400> SEQUENCE: 18

Gly Glu Ala Ala Ala Glu Ala Ala Ala Glu Ala Ala Ala Glu Ala Ala
1               5                   10                  15

Ala Glu Ala Ala Ala Glu Ala Ala Ala Glu Ala Ala Ala Glu Ala Ala
                20                  25                  30

Ala Pro Glu Ala Ala Ala Glu Ala Ala Ala Glu Ala Ala Ala Glu Ala
            35                  40                  45

Ala Ala Glu Ala Ala Ala Glu Ala Ala Ala Glu Ala Ala Ala Glu Ala
        50                  55                  60

Ala Ala Glu Glu Glu Glu Glu
65                  70

<210> SEQ ID NO 19
<211> LENGTH: 51
<212> TYPE: PRT
<213> ORGANISM: Artificial Sequence
<220> FEATURE:
<223> OTHER INFORMATION: synthetic peptide

<400> SEQUENCE: 19

Ala Glu Ala Glu Ala Glu Ala Glu Ala Glu Ala Glu Ala Glu Ala Glu
1               5                   10                  15

Ala Glu Ala Glu Ala Glu Ala Glu Ala Glu Ala Glu Ala Glu Ala Glu
                20                  25                  30

Ala Glu Ala Glu Ala Glu Ala Glu Ala Glu Ala Glu Ala Glu Ala Glu
        35                  40                  45

Ala Glu Lys
    50

<210> SEQ ID NO 20
<211> LENGTH: 73
<212> TYPE: PRT
<213> ORGANISM: Artificial Sequence
<220> FEATURE:
<223> OTHER INFORMATION: synthetic peptide

<400> SEQUENCE: 20

Gly Glu Ala Ala Ala Glu Ala Ala Ala Glu Ala Ala Ala Glu Ala Ala
1               5                   10                  15

Ala Pro Glu Ala Ala Ala Glu Ala Ala Ala Glu Ala Ala Ala Glu Ala
                20                  25                  30

Ala Ala Pro Glu Ala Ala Ala Glu Ala Ala Ala Glu Ala Ala Ala Glu
        35                  40                  45

Ala Ala Ala Pro Glu Ala Ala Ala Glu Ala Ala Ala Glu Ala Ala Ala
    50                  55                  60

Glu Ala Ala Ala Glu Glu Glu Glu Glu
65                  70

<210> SEQ ID NO 21
<211> LENGTH: 70
<212> TYPE: PRT
<213> ORGANISM: Artificial Sequence
<220> FEATURE:
<223> OTHER INFORMATION: synthetic peptide

<400> SEQUENCE: 21

Gly Glu Ala Ala Ala Lys Ala Ala Ala Glu Ala Ala Ala Lys Ala Ala
1               5                   10                  15

Ala Glu Ala Ala Ala Lys Ala Ala Ala Glu Ala Ala Ala Lys Ala Ala
                20                  25                  30

Ala Glu Ala Ala Ala Glu Ala Ala Ala Glu Ala Ala Ala Glu Ala Ala
        35                  40                  45

Ala Glu Ala Ala Ala Glu Ala Ala Ala Glu Ala Ala Ala Glu Ala Ala
    50                  55                  60

Ala Glu Glu Glu Glu Glu
65                  70

<210> SEQ ID NO 22
<211> LENGTH: 70
<212> TYPE: PRT
<213> ORGANISM: Artificial Sequence
<220> FEATURE:
<223> OTHER INFORMATION: synthetic peptide

<400> SEQUENCE: 22

Gly Glu Ala Ala Ala Lys Ala Ala Ala Glu Ala Ala Ala Lys Ala Ala
1               5                   10                  15

Ala Glu Ala Ala Ala Lys Ala Ala Ala Glu Ala Ala Ala Lys Ala Ala
                20                  25                  30

-continued

```
Ala Glu Ala Ala Ala Lys Ala Ala Ala Glu Ala Ala Lys Ala Ala
            35                  40                  45
Ala Glu Ala Ala Ala Lys Ala Ala Ala Glu Ala Ala Lys Ala Ala
    50                  55                  60
Ala Glu Glu Glu Glu Glu
65                  70

<210> SEQ ID NO 23
<211> LENGTH: 70
<212> TYPE: PRT
<213> ORGANISM: Artificial Sequence
<220> FEATURE:
<223> OTHER INFORMATION: synthetic peptide

<400> SEQUENCE: 23

Gly Glu Pro Pro Pro Glu Pro Pro Pro Glu Pro Pro Pro Glu Pro Pro
1               5                   10                  15
Pro Glu Pro Pro Pro Glu Pro Pro Pro Glu Pro Pro Pro Glu Pro Pro
            20                  25                  30
Pro Glu Pro Pro Pro Glu Pro Pro Pro Glu Pro Pro Pro Glu Pro Pro
            35                  40                  45
Pro Glu Pro Pro Pro Glu Pro Pro Pro Glu Pro Pro Pro Glu Pro Pro
    50                  55                  60
Pro Glu Glu Glu Glu Glu
65                  70

<210> SEQ ID NO 24
<211> LENGTH: 70
<212> TYPE: PRT
<213> ORGANISM: Artificial Sequence
<220> FEATURE:
<223> OTHER INFORMATION: synthetic peptide

<400> SEQUENCE: 24

Gly Glu Ala Ala Ala Glu Ala Ala Ala Glu Ala Ala Ala Glu Ala Ala
1               5                   10                  15
Ala Glu Ala Ala Ala Glu Ala Ala Ala Glu Ala Ala Ala Glu Ala Ala
            20                  25                  30
Ala Glu Ala Ala Ala Glu Ala Ala Ala Glu Ala Ala Ala Glu Ala Ala
            35                  40                  45
Ala Glu Ala Ala Ala Glu Ala Ala Ala Glu Ala Ala Ala Glu Ala Ala
    50                  55                  60
Ala Glu Glu Glu Glu Glu
65                  70
```

POLYPEPTIDE TAGGED NUCLEOTIDES AND USE THEREOF IN NUCLEIC ACID SEQUENCING BY NANOPORE DETECTION

TECHNICAL FIELD

This application relates to tagged nucleotide compositions wherein the tag comprises a polypeptide, methods of preparing and using the disclosed polypeptide-tagged nucleotide compositions for sequencing nucleic acids, and in particular, nanopore-based sequencing methods.

REFERENCE TO SEQUENCE LISTING

The official copy of the Sequence Listing is submitted concurrently with the specification as an ASCII formatted text file with a file name of "04338-523US1_PCTSeqList.txt", a creation date of Sep. 13, 2016, and a size of 16,142 bytes. The Sequence Listing filed herewith is part of the specification and is incorporated in its entirety by reference herein.

BACKGROUND

Nucleic acid sequencing is the process for determining the nucleotide sequence of a nucleic acid. Such sequence information may be helpful in diagnosing and/or treating a subject. For example, the sequence of a nucleic acid of a subject may be used to identify, diagnose, and potentially develop treatments for genetic diseases. As another example, research into pathogens may lead to treatment for contagious diseases. Since some diseases are characterized by as little as one nucleotide difference in a chain of millions of nucleotides, highly accurate sequencing is essential.

Single-molecule sequencing-by-synthesis (SBS) techniques using nanopores have been developed. See e.g., US Pat. Publ. Nos. 2013/0244340 A1, 2013/0264207 A1, 2014/0134616 A1. Nanopore SBS involves using a polymerase to synthesize a DNA strand complementary to a target sequence template and concurrently determining the identity of each nucleotide monomer as it is added to the growing strand, thereby determining the target sequence. Each added nucleotide monomer is detected by monitoring current flow through a nanopore located adjacent to the polymerase active site over time as the strand is synthesized. Obtaining an accurate signal requires proper positioning of the polymerase active site near a nanopore, and the use of a tag on each added nucleotide which can enter the nanopore and provide an identifiable change in the current flowing through the pore. In order to provide for accurate nanopore sequencing, it is important for the tag to enter and reside in the nanopore for a sufficient amount of time (i.e., "dwell time"), and while residing in the nanopore, provide for a sufficiently detectable, and identifiable blockage of current through the nanopore (i.e., "blocking current"), such that the specific nucleotide associated with the tag can be distinguished unambiguously from the other tagged nucleotides.

Kumar et al., (2012) "PEG-Labeled Nucleotides and Nanopore Detection for Single Molecule DNA Sequencing by Synthesis," Scientific Reports, 2:684; DOI: 10.1038/srep00684, describes using a nanopore to distinguish four different length PEG-coumarin tags attached via a terminal 5'-phosphoramidate to a dG nucleotide, and separately demonstrates efficient and accurate incorporation of these four PEG-coumarin tagged dG nucleotides by DNA polymerase. See also, US Patent Application Publications US 2013/0244340 A1, published Sep. 19, 2013, US 2013/0264207 A1, published Oct. 10, 2013, and US 2014/0134616 A1, published May 14, 2014.

Stefureac et al. (2006) describes transport of peptides through membranes by α-hemolysin but did not propose the use of this transport phenomenon for sequencing (see e.g., Stefureac et al., "Transport of alpha-helical Peptides through alpha-Hemolysin and Aerolysin Pores," Biochemistry 2006, 45, 9172; Stefureac et al., "Modulation of the translocation of peptides through nanopores by the application of an AC electric field," Chem. Comm. 2012, 48, 1028).

WO 2013/154999 generally describes the use of tagged nucleotides where the tag can include a peptide or amino acids, and specifically provides that the tag has a charge that is reverse in sign to the charge of the rest of the compound. Thus, a peptide tag attached to a nucleotide should have the appropriate number of lysines or arginines to balance the number of phosphates.

WO 2013/191793 discloses generally the use of peptides as nucleotide tags but provides no specific peptide sequences, or properties of such peptide tags.

U.S. Pat. No. 8,652,779 B2 generally describes the possible use of peptides as "charge blockade labels" for nanopore sequencing, and discloses three positively-charged 7-mer and 11-mer peptide blockade labels that have from 6 to 7 lysine residues. U.S. Pat. No. 8,652,779 B2, however, fails to demonstrate that these labels can bind to an actual nanopore-attached polymerase and provide the necessary nanopore current blockage levels and dwell times sufficient for sequencing.

The above-described prior disclosures fail to teach specific polypeptide tag structures that can provide dwell times of sufficient length and blocking currents that are sufficiently narrow and distinguishable to be useful for nanopore sequencing applications. Accordingly, there remains a need for polypeptide-tagged nucleotide compositions and methods that can be used in nanopore and other sequencing techniques.

SUMMARY

The present disclosure provides compositions of polypeptide-tagged nucleotides, and processes for preparing and using such polypeptide-tagged nucleotides, including their use in nanopore sequencing. The polypeptide tags of these tagged nucleotide compounds comprise at least one helical structure and an overall charge. The polypeptide-tagged nucleotides are well-suited for use in nanopore detection systems and provide surprising advantages for nanopore detection including, but not limited to, greater blocking current reductions (relative to open-channel current) with narrower variances, long dwell times, and low background current due to fewer non-specific capture events in the nanopore. Additionally, as described herein, different polypeptide-tagged nucleotides of the present disclosure can provide distinguishable nanopore blocking currents and other nanopore detection characteristics.

In some embodiments, the present disclosure provides a compound of structural formula (I)

$$N\text{-}P\text{-}L\text{-}T \qquad (I)$$

wherein, N is a nucleoside; P is an oligophosphate covalently attached to a 5'-O group of the nucleoside, wherein the oligophosphate consists of 3 to 12 phosphate groups; L is a linker covalently attached to a terminal phosphate group of the oligophosphate; and T is a polypeptide tag covalently attached to the linker, wherein the polypeptide has an overall charge and comprises at least one helical structure.

In some embodiments, the compound of structural formula (I) comprises structural formula (II):

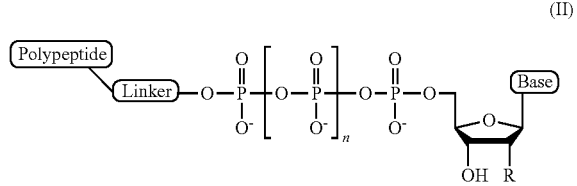

(II)

wherein, Base is selected from adenosine, cytidine, guanosine, thymidine, and uridine; R is selected from H and OH; n is from 1 to 4; Linker is a linker comprising a covalently bonded chain of 2 to 100 atoms; and Polypeptide is a polypeptide tag comprising an overall charge and at least one helical structure.

The present disclosure further provides compounds of various sub-structures encompassed by the structural formulas (I) and (II) which comprise ranges of the various structures including the base, oligophosphate, linker, and polypeptide tag, as disclosed elsewhere herein.

For example, in some embodiments the compound of structural formula (I) or (II) can comprise a polypeptide tag wherein the length of the polypeptide tag ranges from at least 16 amino acid residues to at least 90 amino acid residues, and including various intermediate length ranges as disclosed herein. In some embodiments, the helical structure of the polypeptide tag can comprise from at least 8 amino acid residues to at least 60 amino acid residues, and include various intermediate ranges as disclosed herein. In some embodiments, the helical structure is an α-helix, and optionally, the length of the α-helix is at least 10 amino acid residues, at least 16 amino acid residues, at least 20 amino acid residues, at least 25 amino acid residues, at least 30 amino acid residues, or at least 40 amino acid residues. Additionally, in some embodiments, the α-helix can comprise various sequence motifs including at least 2 repeats of a sequence motif comprising at least 3 amino acid residues, and optionally 2 repeats of the sequence motif wherein the motif comprises at a least 4 amino acid residues, at least 5 amino acid residues, or at least 6 amino acid residues. In some embodiments, the sequence motif is a homopolymer, and optionally the homopolymeric sequence motif can comprise the sequence AAA. In some embodiments, the repeats of the sequence motif are not interrupted by an amino acid residue that is non-helix-forming. In certain embodiments, the sequence motif is selected from the group of motifs consisting of: EAAA, AEAA, AAEA, AAAE, DAAA, ADAA, AADA, AAAD, RAAA, ARAA, AARA, AAAR, KAAA, AKAA, AAKA, and AAAK.

In some embodiments related to the features of the polypeptide tags, the overall charge of the polypeptide tag is negative, optionally wherein the overall charge of the polypeptide tag is between about −10 and −30. In some embodiments of the negatively changed polypeptide tag, at least the three amino acid residues of the polypeptide tag at the terminus distal from the linker are negatively charged residues, and optionally the at least the five amino acid residues of the polypeptide tag at the terminus distal from the linker are negatively charged residues. In certain embodiments, the negatively charged residues are selected from the group consisting of glutamic acid, aspartic acid, gamma-carboxy glutamic acid, homo-glutamic acid, cysteic acid, phospho-serine, phospho-threonine, phospho-tyrosine, and combinations thereof. In some embodiments, the 25% of the amino acid residues located at the end of the polypeptide tag distal from the linker have a net charge absolute value greater than the net charge absolute value of the 25% of the amino acid residues located at the end of the polypeptide tag proximal to the linker.

In some embodiments, the polypeptide tag comprises a polypeptide tag selected from Table 4.

In some embodiments the compound of structural formula (I) or (II) can comprise compounds comprising a range of different linker structures, including but not limited to a compounds of structural formula (III):

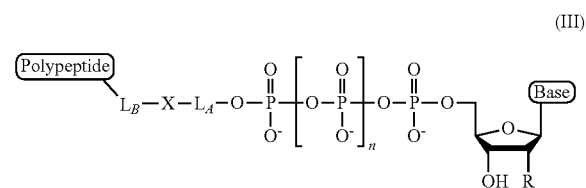

(III)

wherein, "Base" is a naturally occurring or non-naturally occurring nucleobase; R is selected from H and OH; n is from 1 to 10; "Polypeptide" is a polypeptide that has an overall charge and comprises at least one helical structure; and "-$L_B$-X-$L_A$-" is a linker wherein, $L_A$ and $L_B$ each comprise a covalently bonded chain of 2 to 100 atoms; and X is a chemical moiety selected from the group consisting of ester, ether, thioether, amine, amide, imide, carbonate, carbamate, squarate, thiazole, thiazolidine, hydrazone, oxime, triazole, and dihydropyridazine. In some embodiments of the compound of structural formula (III), $L_A$ and $L_B$ each independently comprises a linker structure selected from structural formulas (XVIIIa)-(XVIIId). In some embodiments, $L_B$ comprises an amino acid residue, and optionally, $L_B$ can comprise an amino acid residue at the N-terminus or the C-terminus of the polypeptide tag.

The present disclosure also provides methods for preparing a compound of any one of structural formulas (I) or (II), or any of the various sub-structures encompassed by the structural formulas (I) and (II) comprising ranges of the various structures including the base, oligophosphate, linker, and polypeptide tag, as disclosed herein.

The present disclosure also provides a composition comprising a set of tagged nucleotides each with a different tag, wherein each different tag causes a different blocking current when it is situated in the nanopore, and the set comprises at least one compound of any one of structural formulas (I) or (II), or any of the various sub-structures encompassed by the structural formulas (I) and (II) comprising ranges of the various structures including the base, oligophosphate, linker, and polypeptide tag, as disclosed herein.

The present disclosure also provides a method for determining the sequence of a nucleic acid which utilizes at least one compound of any one of structural formulas (I) or (II), or any of the various sub-structures encompassed by the structural formulas (I) and (II) comprising ranges of the various structures including the base, oligophosphate, linker, and polypeptide tag, as disclosed herein. Thus, in some embodiments the present disclosure provides a method comprising: (a) providing a nanopore sequencing composition comprising: a membrane, an electrode on the cis side and the trans side of the membrane, a nanopore with its pore extending through the membrane, an electrolyte solution in contact with both electrodes, an active polymerase situated adjacent to the nanopore, and a primer strand complexed with the polymerase; (b) contacting the nanopore sequencing composition with (i) a strand of the nucleic acid; and (ii) a set of tagged nucleotides each with a different tag, wherein each different tag causes a different blocking current and/or has a different dwell time when it is situated in the nanopore, and the set comprises at least one compound of structural formulas (I) or (II), including any of the various substructures encompassed by structural formulas (I) and (II) comprising ranges of the various structures including the base, oligophosphate, linker, and polypeptide tag, as disclosed herein; and (c) detecting the different blocking currents and/or blocking voltages and/or different dwell times of the tags over time and correlating to each of the different tagged nucleotides incorporated by the polymerase which are complimentary to the nucleic acid sequence, and thereby determining the nucleic acid sequence.

DETAILED DESCRIPTION

Figure 1:
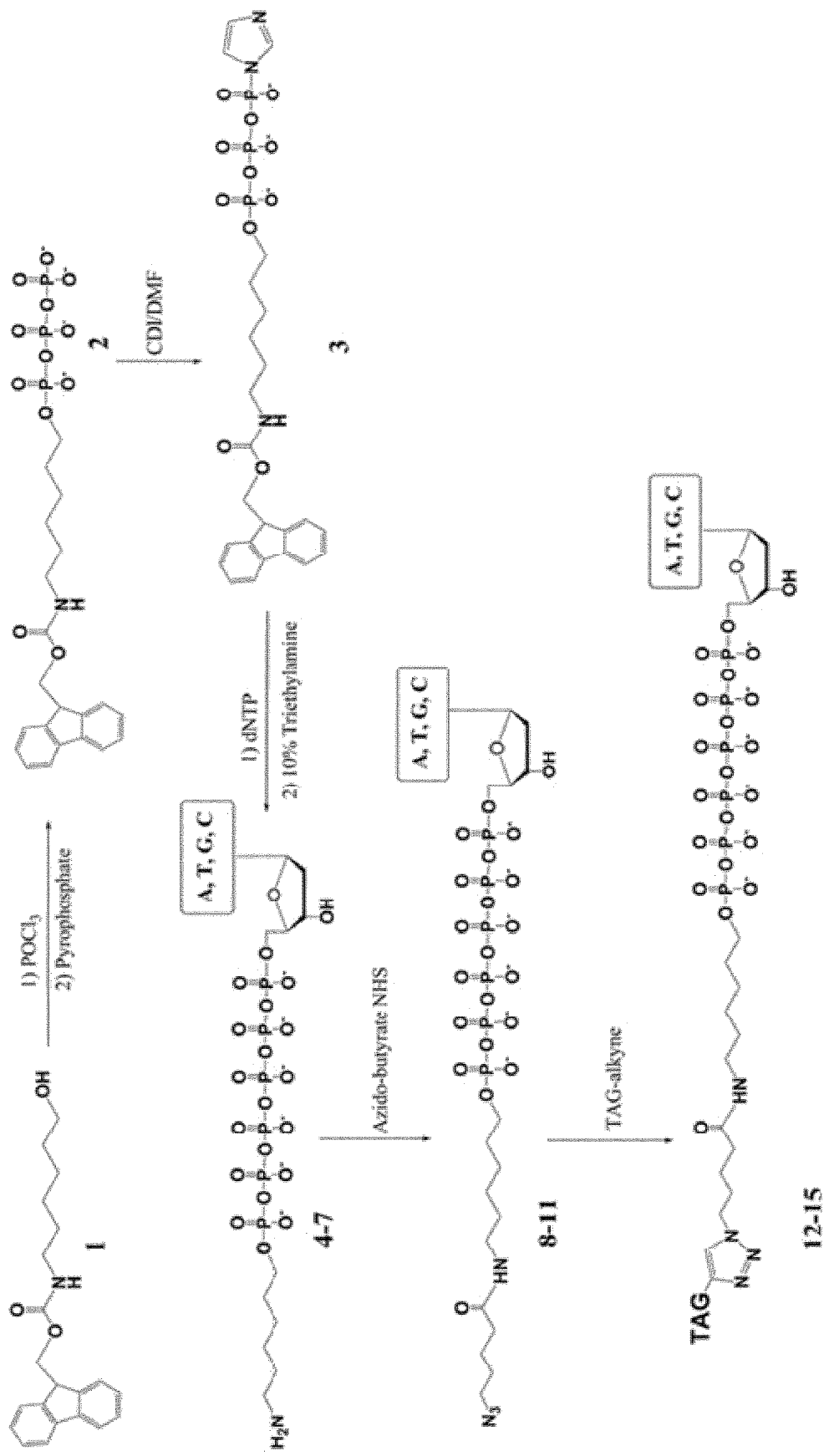
FIG. 1 depicts a synthetic reaction scheme useful for preparing a polypeptide-tagged nucleoside-hexaphosphate via an azido-alkyne click reaction.

For the descriptions herein and the appended claims, the singular forms "a", and "an" include plural referents unless the context clearly indicates otherwise. Thus, for example, reference to "a protein" includes more than one protein, and reference to "a compound" refers to more than one compound. The use of "comprise," "comprises," "comprising" "include," "includes," and "including" are interchangeable and not intended to be limiting. It is to be further understood that where descriptions of various embodiments use the term "comprising," those skilled in the art would understand that in some specific instances, an embodiment can be alternatively described using language "consisting essentially of" or "consisting of."

Where a range of values is provided, unless the context clearly dictates otherwise, it is understood that each intervening integer of the value, and each tenth of each intervening integer of the value, unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding (i) either or (ii) both of those included limits are also included in the invention. For example "1 to 50" includes "2 to 25", "5 to 20", "25 to 50", "1 to 10", etc.

It is to be understood that both the foregoing general description, including the drawings, and the following detailed description are exemplary and explanatory only and are not restrictive of this disclosure.

Definitions

The technical and scientific terms used in the descriptions herein will have the meanings commonly understood by one of ordinary skill in the art, unless specifically defined otherwise. Accordingly, the following terms are intended to have the following meanings.

"Nucleic acid," as used herein, refers to a molecule of one or more nucleic acid subunits which comprise one of the nucleobases, adenine (A), cytosine (C), guanine (G), thymine (T), and uracil (U), or variants thereof. Nucleic acid can refer to a polymer of nucleotides (e.g., dAMP, dCMP, dGMP, dTMP), also referred to as a polynucleotide or oligonucleotide, and includes DNA, RNA, in both single and double-stranded form, and hybrids thereof.

"Nucleotide," as used herein refers to a nucleoside-5'-oligophosphate compound, or structural analog of a nucleoside-5'-oligophosphate, which is capable of acting as a substrate or inhibitor of a nucleic acid polymerase.

Exemplary nucleotides include, but are not limited to, nucleoside-5'-triphosphates (e.g., dATP, dCTP, dGTP, dTTP, and dUTP); nucleosides (e.g., dA, dC, dG, dT, and dU) with 5'-oligophosphate chains of 4 or more phosphates in length (e.g., 5'-tetraphosphate, 5'-pentaphosphate, 5'-hexaphosphate, 5'-heptaphosphate, 5'-octaphosphate); and structural analogs of nucleoside-5'-triphosphates that can have a modified base moiety (e.g., a substituted purine or pyrimidine base), a modified sugar moiety (e.g., an O-alkylated sugar), and/or a modified oligophosphate moiety (e.g., an oligophosphate comprising a thiophosphate, a methylene, and/or other bridges between phosphates).

"Nucleotide analog," as used herein refers to a chemical compound that is structurally similar to a nucleotide and capable of serving as a substrate or inhibitor of a nucleic acid polymerase. A nucleotide analog may have a modified or non-naturally occurring nucleobase moiety, a modified sugar, and/or a modified oligophosphate moiety.

Nucleoside," as used herein, refers to a molecular moiety that comprises a naturally occurring or non-naturally occurring nucleobase attached to a sugar moiety (e.g., ribose or deoxyribose).

"Deoxynucleoside," as used herein, refers to a molecular moiety that comprises a sugar moiety with a single hydroxyl group (e.g., deoxyribose or deoxyhexose group) to which is attached a naturally occurring or non-naturally occurring nucleobase.

"Oligophosphate," as used herein, refers to a molecular moiety that comprises an oligomer of phosphate groups. For example, an oligophosphate can comprise an oligomer of from 2 to 20 phosphates, an oligomer of from 3 to 12 phosphates, an oligomer of from 3 to 9 phosphates.

"Polymerase," as used herein, refers to any natural or non-naturally occurring enzyme or other catalyst that is capable of catalyzing a polymerization reaction, such as the polymerization of nucleotide monomers to form a nucleic acid polymer. Exemplary polymerases that may be used in the compositions and methods of the present disclosure include the nucleic acid polymerases such as DNA polymerase (e.g., enzyme of class EC 2.7.7.7), RNA polymerase (e.g., enzyme of class EC 2.7.7.6 or EC 2.7.7.48), reverse transcriptase (e.g., enzyme of class EC 2.7.7.49), and DNA ligase (e.g., enzyme of class EC 6.5.1.1).

"Nanopore," as used herein, refers to a pore, channel, or passage formed or otherwise provided in a membrane or other barrier material that has a characteristic width or diameter of about 0.1 nm to about 1000 nm. A nanopore can be made of a naturally-occurring pore-forming protein, such as α-hemolysin from *S. aureus*, or a mutant or variant of a wild-type pore-forming protein, either non-naturally occurring (i.e., engineered) such as α-HL-C46, or naturally occurring. A membrane may be an organic membrane, such as a lipid bilayer, or a synthetic membrane made of a non-naturally occurring polymeric material. The nanopore may be disposed adjacent or in proximity to a sensor, a sensing circuit, or an electrode coupled to a sensing circuit, such as, for example, a complementary metal-oxide semiconductor (CMOS) or field effect transistor (FET) circuit.

"Pore-forming protein," as used herein refers to a natural or non-naturally occurring protein capable of forming a pore or channel structure in a barrier material such as a lipid bilayer or cell membrane. The terms as used herein are intended to include both a pore-forming protein in solution, and a pore-forming protein embedded in a membrane or barrier material, or immobilized on a solid substrate or support. The terms as used herein are intended to including pore-forming proteins as monomers and also as any multimeric forms into which they are capable of assembling. Exemplary pore-forming proteins that may be used in the compositions and methods of the present disclosure include α-hemolysin (e.g., from *S. aureus*), β-hemolysin, γ-hemolysin, aerolysin, cytolysin (e.g., pneumolysin), leukocidin, melittin, and porin A (e.g., MspA from *Mycobacterium smegmatis*).

"Tag," as used herein, refers to a molecule that enables or enhances the ability to detect and/or identify, either directly or indirectly, a molecule or molecular complex, which is coupled to the tag. For example, the tag can provide a detectable property or characteristic, such as steric bulk or volume, electrostatic charge, electrochemical potential, and/or spectroscopic signature.

"Tagged nucleotide," as used herein refers to a nucleotide or nucleotide analog with a tag attached to the oligophosphate moiety, base moiety, or sugar moiety.

"Nanopore-detectable tag" as used herein refers to a tag that can enter into, become positioned in, be captured by, translocate through, and/or traverse a nanopore and thereby result in a detectable change in current through the nanopore. Exemplary nanopore-detectable tags include, but are not limited to, natural or synthetic polymers, such as polyethylene glycol, oligonucleotides, polypeptides, carbohydrates, peptide nucleic acid polymers, locked nucleic acid polymers, any of which may be optionally modified with or linked to chemical groups, such as dye moieties, or fluorophores, that can result in detectable nanopore current changes.

"Linker," as used herein, refers to any molecular moiety that provides a bonding attachment with some space between two or more molecules, molecular groups, and/or molecular moieties.

"Peptide," as used herein, refers to at least two amino acids covalently linked by an amide bond.

"Amino acid," as used herein, refers to a compound comprising amine and carboxylic functional groups, and a side-chain. Amino acids can include the standard, 20 genetically encoded α-amino acids, as well as any other naturally-occurring and synthetic amino acids, known in the art and/or disclosed herein, which are capable of undergoing a condensation reaction with another amino acid to form a peptide.

"Polypeptide," as used herein, refers to a polymer of from 2 to about 400 or more amino acids. When polypeptide sequences are presented herein as a string of one-letter or three-letter abbreviations (or mixtures thereof), the sequences are presented in the amino (N) to carboxy (C) direction in accordance with common convention.

"Helical structure," as used herein, refers to an oligomer or polymer of amino acids that forms one or more three-dimensional spiral or loop structures, such as an α-helix structure.

"Overall charge," as used herein in the context of polypeptide tags refers to the sum of the positively charged and negatively charged side-chains of the amino acid residues that make up the polypeptide tag. For example, a polypeptide tag comprising a polypeptide having 5 lysine residues, which are positively charged (+1), and 15 glutamic acid residues, which are negatively charged (−1), has an overall charge of −10.

"Background current" as used herein refers to the current level measured across a nanopore when a potential is applied and the nanopore is open and unblocked (e.g., there is no tag in the nanopore).

"Blocking current" as used herein refers to the current level measured across a nanopore when a potential is applied and a tag is present the nanopore. Generally, the presence of the tag molecule in the nanopore restrict the flow of charged molecules through the nanopore thereby altering the current level from the background.

"Blocking voltage" as used herein refers to the voltage level measured across a nanopore when a current is applied and a tag is present the nanopore. Generally, the presence of the tag molecule in the nanopore restrict the flow of charged molecules through the nanopore thereby altering the voltage level from the background "Dwell time" as used herein in the context of capture of a tag in a nanopore refers to the time that the tag spends in the nanopore as detected by a blocking current.

"Naturally occurring" refers to the form found in nature. For example, a naturally occurring or wild-type protein is a protein having a sequence present in an organism that can be isolated from a source found in nature, and which has not been intentionally modified by human manipulation.

"Non-naturally occurring" or "recombinant" or "engineered" or when used with reference to, e.g., nucleic acid, polypeptide, or a cell, refers to a material that has been modified in a manner that would not otherwise exist in nature, or is identical thereto but produced or derived from synthetic materials and/or by manipulation using recombinant techniques. Non-limiting examples include, among others, recombinant cells expressing genes that are not found within the native (non-recombinant) form of the cell or express native genes that are otherwise expressed at a different level.

DETAILED DESCRIPTION OF EMBODIMENTS

In a first aspect, the present invention provides a compound of structural formula (I)

$$\text{N-P-L-T} \quad (I)$$

wherein,
- N is a nucleoside;
- P is an oligophosphate covalently attached to a 5'-O group of the nucleoside, wherein the oligophosphate consists of 3 to 12 phosphate groups;
- L is a linker covalently attached to a terminal phosphate group of the oligophosphate; and
- T is a polypeptide tag covalently attached to the linker, wherein the polypeptide has an overall charge and comprises at least one helical structure.

Preferably, the compound comprises structural formula (II):

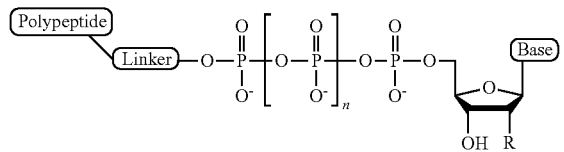

(II)

wherein,
- Base is selected from adenosine, cytidine, guanosine, thymidine, and uridine;
- R is selected from H and OH;
- n is from 1 to 4;
- Linker is a linker comprising a covalently bonded chain of 2 to 100 atoms; and
- Polypeptide is a polypeptide tag comprising an overall charge and at least one helical structure.

The length of the polypeptide tag may be at least 16 amino acid residues at least 20 amino acid residues, at least 25 amino acid residues, at least 30 amino acid residues, at least 40 amino acid residues, at least 50 amino acid residues, at least 60 amino acid residues, at least 70 amino acid residues, at least 80 amino acid residues, or at least 90 amino acid residues. The helical structure may comprise is at least 8 amino acid residues, optionally at least 16 amino acid residues, at least 20 amino acid residues, at least 25 amino acid residues, at least 30 amino acid residues, at least 40 amino acid residues, at least 50 amino acid residues, or at least 60 amino acid residues. For example, at least 50% or at least 75% of the amino acid residues are A residues.

The helical structure may be an α-helix, wherein the length of the α-helix is at least 10 amino acid residues, at least 16 amino acid residues, at least 20 amino acid residues, at least 25 amino acid residues, at least 30 amino acid residues, or at least 40 amino acid residues. Said α-helix may comprise at least 2 repeats of a sequence motif comprising at least 3 amino acid residues, at a least 4 amino acid residues, at least 5 amino acid residues, or at least 6 amino acid residues. The sequence motif may be a homopolymer, which may comprise the sequence AAA. Said repeats may not be interrupted by an amino acid residue that is non-helix-forming. In one embodiment said sequence motif consists of 4 amino acids, which may comprise at least two A residue or three A residues and a charged amino acid residue. For example, the 4 amino acid sequence motif is selected from the group of motifs consisting of: EAAA, AEAA, AAEA, AAAE, DAAA, ADAA, AADA, AAAD, RAAA, ARAA, AARA, AAAR, KAAA, AKAA, AAKA, and AAAK or comprises at least two A residues, a charged amino acid residue, and an amino acid selected from the group consisting of F, H, I, L, M, T, W, and Y. Said repeats may not be interrupted by an amino acid residue that is non-helix-forming.

The overall charge of the polypeptide tag may be negative, for example, the overall charge of the polypeptide tag is between about −10 and −30. The at least three, four or five amino acid residues of the polypeptide tag at the terminus distal from the linker may be negatively charged residues. The negatively charged residues are selected from the group consisting of glutamic acid, aspartic acid, gamma-carboxy glutamic acid, homo-glutamic acid, cysteic acid, phosphoserine, phospho-threonine, phospho-tyrosine, and combinations thereof. Overall, 25% of the amino acid residues located at the end of the polypeptide tag distal from the linker may have a net charge absolute value greater than the net charge absolute value of the 25% of the amino acid residues located at the end of the polypeptide tag proximal to the linker. In certain embodiments, the polypeptide tag comprises a polypeptide tag selected from Table 4.

Element "P" may consist of from 3 to 9 phosphate groups, optionally from 4 to 6 phosphate groups, or optionally 6 phosphate groups. The linker "L" may comprise a chemical group selected from the group consisting of: ester, ether, thioether, amine, amide, imide, carbonate, carbamate, squarate, thiazole, thiazolidine, hydrazone, oxime, triazole, dihydropyridazine, phosphodiester, polyethylene glycol (PEG), and combinations thereof. Preferably, the linker comprises a chemical group selected from the group consisting of a triazole, a dihydropyridazine, an amide, a thioether, an ether, an ester, a phosphodiester, a carbonate, a carbamate, a squarate, a thiazole, a thiazolidine, a hydrazone, and an oxime. In one embodiment, the linker comprises a triazole group generated by reaction of an azide group with an alkyne group.

The compound according to the invention may also comprise structural formula (III):

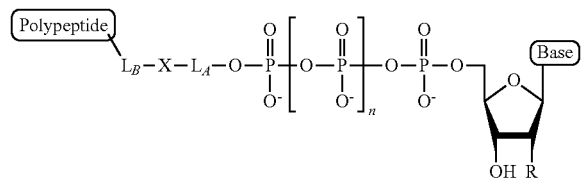

(III)

wherein,
- "Base" is a naturally occurring or non-naturally occurring nucleobase;
- R is selected from H and OH; n is from 1 to 10;
- "Polypeptide" is a polypeptide that has an overall charge and comprises at least one helical structure; and
- "-$L_B$-X-$L_A$-" is a linker wherein,
  - $L_A$ and $L_B$ each comprise a covalently bonded chain of 2 to 100 atoms; and X is a chemical moiety selected from the group consisting of ester, ether, thioether, amine, amide, imide, carbonate, carbamate, squarate, thiazole, thiazolidine, hydrazone, oxime, triazole, and dihydropyridazine.

$L_A$ and $L_B$ each independently may comprise a chemical moiety selected from the group consisting of: linear ($C_1$-$C_{12}$) alkyl, linear ($C_1$-$C_{12}$) alkene, linear ($C_1$-$C_{12}$) alkyne, ester, ether, thioether, amine, amide, imide, carbonate, carbamate, squarate, thiazole, thiazolidine, hydrazone, oxime, triazole, dihydropyridazine, phosphodiester, polyethylene glycol (PEG), and combinations thereof. $L_a$ may comprise an amino acid residue. $L_B$ may comprise an amino acid residue at the N-terminus or the C-terminus of the polypeptide tag.

Examples for compounds according to the present invention are as follows:

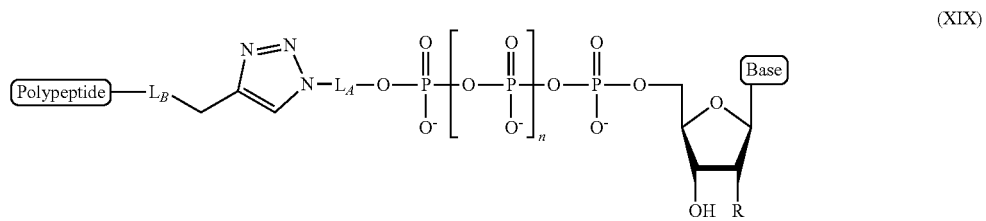

(XIX)

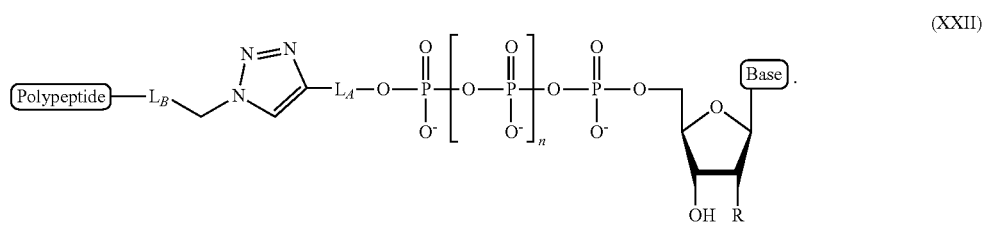

(XXII)

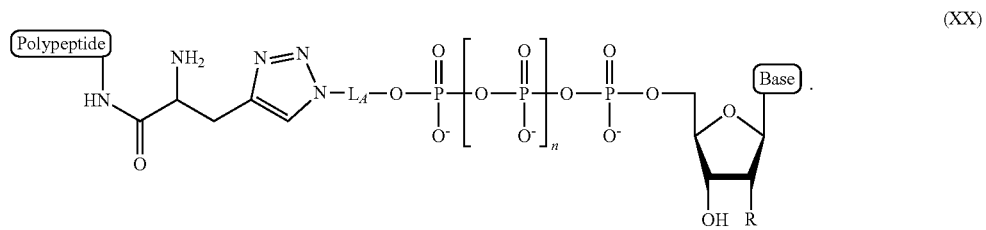

(XX)

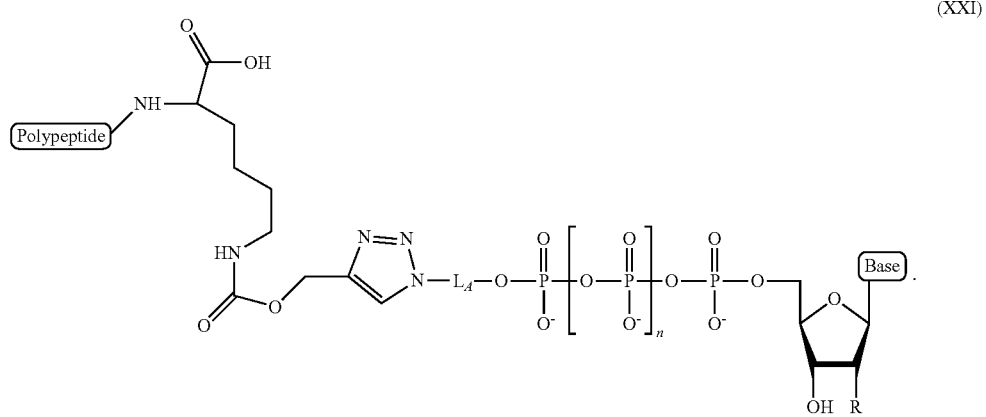

(XXI)

In a second aspect, the present invention provides method of preparing a polypeptide-tagged nucleotide compound of structural formula (II)

(II)

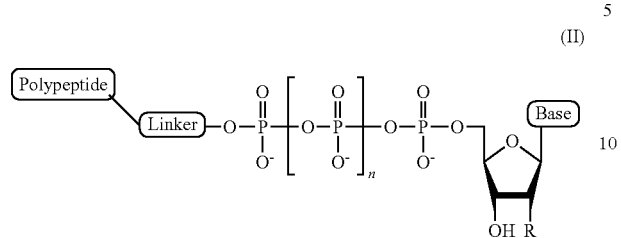

wherein,
  Base is selected from adenosine, cytidine, guanosine, thymidine, and uridine;
  R is selected from H and OH;
  n is from 1 to 4;
  Linker is a linker comprising a covalently bonded chain of 2 to 100 atoms; and
  Polypeptide is a polypeptide tag comprising an overall charge and at least one helical structure
wherein the method comprises the following steps:
(a) providing (i) a nucleotide with from 3 to 12 phosphates attached to its 5'-position, wherein the terminal phosphate is coupled to a first linker forming group; and (ii) a polypeptide tag, wherein the polypeptide tag comprises at least one helical structure, has an overall charge, and is coupled to a second linker forming group, that is capable of reacting with the first linker forming group to form a linker;
wherein
  (1) the first linker forming group is selected from the compounds of structural formulas (IVa)-(XVIIa) and the second linker forming group is the corresponding reactive compound of structural formulas (IVb)-(XVIIb); or
  (2) the first linker forming group is selected from the compounds of structural formulas (IVb)-(XVIIb) and the second linker forming group is the corresponding reactive compound of structural formulas (IVa)-(XVIIa); and
(b) reacting the first linker forming group with the second linker forming group, thereby forming a covalent linkage between the nucleotide to the polypeptide tag.
The first linker forming group may be selected from the group consisting of an alkyne and a diene, and the second linker forming group is selected from the group consisting of an azide and a tetrazine; or (2) the first linker forming group is selected from the group consisting of an azide and a tetrazine, and the second linker forming group is selected from the group consisting of an alkyne and a diene. In one embodiment, the first linker forming group is an azide and the second linker forming group is an alkyne.
In a third aspect, the present invention provides a composition comprising a set of tagged nucleotides each with a different tag, wherein each different tag causes a different blocking current when it is situated in the nanopore, and the set comprises at least one compound as disclosed above.
In a further aspect, the present invention provides a method for determining the sequence of a nucleic acid comprising:
  (a) providing a nanopore sequencing composition comprising: a membrane, an electrode on the cis side and the trans side of the membrane, a nanopore with its pore extending through the membrane, an electrolyte solution in contact with both electrodes, an active polymerase situated adjacent to the nanopore, and a primer strand complexed with the polymerase;
  (b) contacting the nanopore sequencing composition with (i) a strand of the nucleic acid; and (ii) a set of tagged nucleotides each with a different tag, wherein each different tag causes a different blocking current and/or has a different dwell time when it is situated in the nanopore, and the set comprises at least one compound of any as disclosed above; and
  (c) detecting the different blocking currents and/or different dwell times of the tags over time and correlating to each of the different tagged nucleotides incorporated by the polymerase which are complimentary to the nucleic acid sequence, and thereby determining the nucleic acid sequence.

Overview: Tagged Nucleotides and Nanopore Sequencing

The present disclosure describes compositions of polypeptide-tagged nucleotide compounds and related methods, devices, and systems that are useful for nanopore sequencing of nucleic acids. The polypeptide-tagged nucleotides can be used in methods to accurately detect individual nucleotide incorporation by a nucleic acid polymerase into a growing strand that is complementary to a template nucleic acid strand. Generally, the strand extending enzyme (e.g., DNA polymerase) specifically binds a polypeptide-tagged nucleotide that is complimentary to a template nucleic acid strand which is hybridized to the growing nucleic acid strand at its active site. The strand extending enzyme then catalytically couples (i.e., incorporates) the polypeptide-tagged complimentary nucleotide to the end of the growing nucleic acid strand. Completion of the catalytic incorporation event results in the release of the polypeptide tag and oligophosphate moiety (minus the one phosphate incorporated in the growing strand) which then passes through the adjacent nanopore.

Even before it undergoes catalytic process that releases it from the incorporated nucleotide however, the tag of a tagged-nucleotide can enter the pore of the nanopore thereby altering the background current of the nanopore under a potential and causing a blocking current that can be detected. Various molecular properties of the tag (e.g., mass, volume, 3-D structure, electrostatic charge) can greatly affect its interaction with the pore and thereby allow for different tag molecules that have specific, distinguishable signatures for nanopore detection. A variety of nanopore systems and methods for using them to detect tagged molecules including tagged nucleotides in sequencing are known in the art.

See, for example, U.S. patent application Ser. No. 12/308, 091, Ju et al., filed May 18, 2009; U.S. patent application Ser. No. 13/994,431, Ju et al., filed Jun. 14, 2013; US Patent Application Publications US 2013/0244340 A1, published Sep. 19, 2013, US 2013/0264207 A1, published Oct. 10, 2013, and US 2014/0134616 A1, published May 14, 2014; PCT International Publication No. PCT/US13/35635, Ju et al., filed Apr. 8, 2013; and PCT International Publication No. PCT/US13/35640, Ju et al., filed Apr. 8, 2013, each of which is hereby incorporated herein by reference in its entirety.

In most embodiments, nanopore sequencing uses a mixture of four nucleotide analogs (e.g., dA6P, dC6P, dG6P, and dT6P) that can be incorporated by an enzyme into a growing strand, each nucleotide analog having a covalently attached tag that provides an identifiable, and distinguishable signature when detected with a nanopore.

Polypeptide molecules are polymers of amino acids. The wide range of naturally occurring and non-naturally occurring amino acids available and the ease with which they can be synthesized into different polypeptide sequences allow for the generation of polypeptide tags having an extremely wide range of molecular properties that can provide distinguishable nanopore detection.

The present disclosure provides polypeptide-tagged nucleotides where the polypeptide tags feature a variety of distinct molecular characteristics including, but not limited to, varied length of the amino acid chain, volume, 3-D structure (e.g., α-helix), and overall charge.

Polypeptide-Tagged Nucleotide Compound Structures

In some embodiments, the present disclosure provides a polypeptide-tagged nucleotide that is a compound of the general structure (I)

N-P-L-T       (I)

wherein, N is a nucleoside; P is an oligophosphate covalently attached to a 5'-O group of the nucleoside, wherein the oligophosphate comprises 3 to 12 phosphate groups; L is a linker covalently attached to a terminal phosphate group of the oligophosphate; and T is a polypeptide tag covalently attached to the linker, wherein the polypeptide has an overall charge and comprises at least one helical structure.

The nucleoside (N) can be any nucleoside capable of being incorporated by a strand-extending enzyme, such as a polymerase, when the nucleoside is covalently coupled to an oligophosphate (P), such as a triphosphate. The nucleoside can comprise a naturally occurring or non-naturally occurring nucleobase, and a naturally occurring or non-naturally occurring sugar moiety, such as a ribose or deoxyribose group. In some embodiments, the nucleobase is selected from group consisting of adenosine, cytidine, guanosine, thymidine, and uridine. The sugar moiety should provide a free hydroxyl group at a position (e.g., a 3'-OH group) that can form a phosphodiester bond with a growing polynucleotide strand when catalytically incorporated by a strand extending enzyme. The nucleoside sugar moiety should also provide a group allowing covalent attachment of an oligophosphate moiety (e.g., a 5'-O group).

In some embodiments, the polypeptide-tagged nucleotide can comprise a compound, wherein the compound comprises a structure of formula (II):

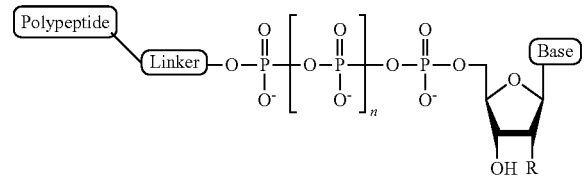

(II)

wherein, "Base" is a naturally occurring or non-naturally occurring nucleobase; R is selected from H and OH; n is from 1 to 10; "Linker" is a linker comprising a covalently bonded chain of 2 to 100 atoms; and "Polypeptide" is a polypeptide that has an overall charge and comprises at least one helical structure.

In some embodiments, the nucleobase ("Base") can be any naturally or non-naturally occurring (e.g., chemically modified) base which is capable of being incorporated by a strand-extending enzyme, such as a polymerase. In some embodiments, the nucleobase is selected from group consisting of adenosine, cytidine, guanosine, thymidine, and uridine.

In some embodiments, the oligophosphate (P) of the polypeptide-tagged nucleotide can be any oligophosphate moiety which, when attached to the 5'-O of the nucleoside, allows the resulting nucleotide to still be capable of being incorporated by a strand-extending enzyme, such as a polymerase. Generally, strand-extending enzymes, such as polymerase, are capable of incorporating nucleotides comprising oligophosphates having chains of from 3 to 12 phosphate groups. Accordingly, in a polypeptide-tagged nucleotide compound of the present disclosure (e.g., the compound of structural formula (I) or (II)) the oligophosphate (P) group can comprise 3 to 12 phosphate groups. As depicted in in the compound of structural formula (II), the oligophosphate of 3 to 12 phosphate groups would be represented by values of n=1 to n=10. Thus, in some embodiments of the present disclosure, the polypeptide-tagged nucleotide compound comprises an oligophosphate (P) group comprising 3 to 9 phosphate groups (or n=1 to 7 for formula (II)). In some embodiments, the oligophosphate group comprises 4 to 6 phosphate groups (or n=2 to 4 for formula (II)). In some embodiments, the oligophosphate group comprises 6 phosphate groups (or n=4 for formula (II)).

In other embodiments, the polypeptide-tagged nucleotides of the present disclosure comprise oligophosphate chains of 4 to 20 phosphates, 4 to 12 phosphates, 4 to 9 phosphates, 4 to 6 phosphates, wherein the chain is attached at the 5' position of the nucleoside (e.g., 5'-tetraphosphate, 5'-pentaphosphate, 5'-hexaphosphate, 5'-heptaphosphate, 5'-octaphosphate, 5'-nonaphosphate, 5'-decaphosphate, etc.).

It is further contemplated that in the polypeptide-tagged nucleotide compounds of the present disclosure, the oligophosphate can include modified phosphate groups, phosphate analogs, or other non-phosphate chemical groups. Of course, the inclusion of such phosphate groups into the oligophosphate should allow the resulting nucleotide to still be capable of being incorporated by a strand-extending enzyme when the oligophosphate is attached to the 5'-O of the nucleoside. Typically, this requires a naturally occurring phosphate group at the α-position and a phosphodiester bond between the α-position and β-positions of the oligophosphate that can undergo the catalytic incorporation by a strand-extending enzyme. Thus, in some embodiments, the oligophosphate can comprise a thiophosphate group. Additionally, it is contemplated that the oligophosphate can include an oligomer of phosphate or phosphate-analog groups with one or more non-phosphate groups, such as a methylene, and/or a bridging group between two or more phosphate groups.

A wide range of linkers can be used in the polypeptide-tagged nucleotide compounds of structural formulas (I) and (II). Generally, the linker can comprise any molecular moiety that is capable of providing a covalent coupling and a desired spacing or structure between the polypeptide tag and the nucleotide. The desired spacing or structure can be selected and optimized for the specific use of the polypeptide-tagged nucleotide compound. For example, in a nanopore detection use, a linker can be selected that provides a spacing that allows the polypeptide tag to enter and reside in the nanopore when the nucleotide forms the ternary complex with an adjacent polymerase. Depending on how the polymerase is coupled to the nanopore, a slightly shorter or longer spacing may be selected so as to provide a suitable blocking current when the polypeptide tag is situation in the pore. Generally, however, the linkers useful in the polypeptide-tagged nucleotide compounds of the present disclosure (e.g., compounds of formulas (I) and (II)) comprise a covalently bonded chain of 2 to 100 atoms. In some embodiments, the linker chain of 2 to 100 atoms comprises one or more chemical moieties selected from the group consisting of: linear ($C_1$-$C_{12}$) alkyl, linear ($C_1$-$C_{12}$) alkene, linear ($C_1$-$C_{12}$) alkyne, ester, ether, thioether, amine, amide, imide, carbonate, carbamate, squarate, thiazole, thiazolidine, hydrazone, oxime, triazole, dihydropyridazine, phosphodiester, polyethylene glycol (PEG), and combinations thereof. A variety of linkers comprising a range of chemical moieties that are useful in the polypeptide-tagged nucleotide compounds are described and exemplified herein.

Typically, the linker is formed during the preparation of a polypeptide-tagged nucleotide compounds of structural formula (I) or (II), in a chemical reaction that covalent couples the polypeptide tag to the oligophosphate moiety. More specifically, this chemical reaction typically involves a polypeptide tag modified with a reactive linker-forming group and a nucleotide comprising an oligophosphate, wherein the terminus of the oligophosphate is also modified with a reactive linker-forming group. This linker forming chemical reaction can be depicted as in Scheme 1.

Accordingly, in some embodiments, the linker comprises a chemical moiety, X, produced in the linker forming reaction between the linker forming reagents, $X_A$ and $X_B$, wherein X is a chemical moiety selected from the group consisting of ester, ether, thioether, amine, amide, imide, carbonate, carbamate, squarate, thiazole, thiazolidine, hydrazone, oxime, triazole, dihydropyridazine, phosphodiester, and polyethylene glycol (PEG).

The chemical moieties, $L_A$ and $L_B$ are chemical groups which can effectively act as linkers or spacers between the polypeptide tag or oligophosphate and their linker forming groups, $X_A$ and $X_B$. Typically, $L_A$ and $L_B$ are chemical moieties that do not react in the linker forming reaction but which provide additional spacing or structure for the final formed linker. The $L_A$ and $L_B$ moieites can be the same or different. In some embodiments, $L_A$ or $L_B$ can be much longer or shorter than the other, and/or provide different structural features, for example features that result in more or less conformational flexibility. Accordingly, in some embodiments, $L_A$ and $L_B$ moieties useful in the polypeptide- Scheme 1

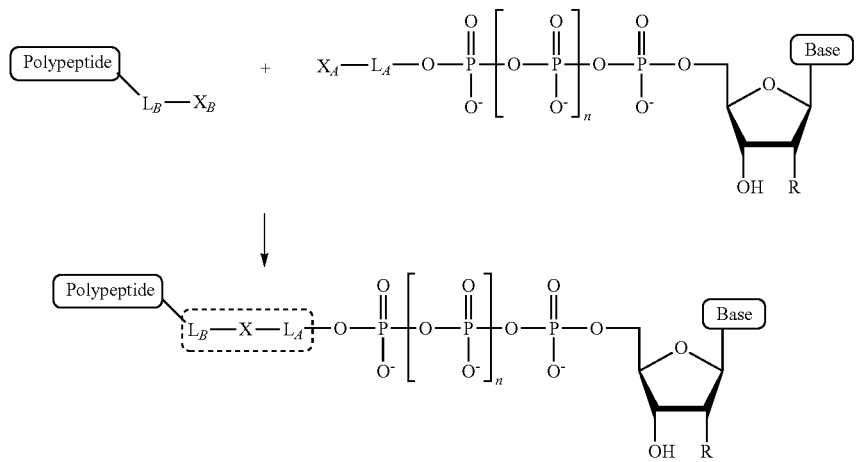

tagged nucleotide compounds of the present disclosure comprise a covalently bonded chain of 2 to 100 atoms, and optionally, one or more chemical moieties selected from the group consisting of: linear ($C_1$-$C_{12}$) alkyl, linear ($C_1$-$C_{12}$) alkene, linear ($C_1$-$C_{12}$) alkyne, ester, ether, thioether, amine, amide, imide, carbonate, carbamate, squarate, thiazole, thiazolidine, hydrazone, oxime, triazole, dihydropyridazine, phosphodiester, polyethylene glycol (PEG), and combinations thereof.

Thus, in some embodiments, the present disclosure provides a polypeptide-tagged nucleotide compound of structural formula (III)

As depicted in Scheme 1, $X_A$ and $X_B$ are the reactive linker forming groups, and $L_A$ and $L_B$, are chemical moieties that precursor linkers to the finally formed linker of structure -$L_B$-X-$L_A$-. Thus, $X_A$ and $X_B$ are chemical moieties which are capable of undergoing a chemical reaction that results in a covalent coupling between the polypeptide tag and the nucleotide. The product of this covalent coupling reaction between the linker forming groups, $X_A$ and $X_B$, is a linker between the polypeptide tag and the nucleotide comprising a general structure -$L_B$-X-$L_A$-. That is, in some embodiments, the linker "L" or "Linker" as in the compounds of formula (I) and (II) is a linker of structural formula "-$L_B$-X-$L_A$-" as depicted in Scheme 1.

The new chemical moiety, X, is the distinctive chemical moiety produced in the linker forming reaction. Often, the name of the particular chemical group X is used to denote the type of linker, although the other parts of the linker provided by $L_A$ and $L_B$ may contribute substantially to the overall structure of the linker. For example, a characteristic linker moiety X can be a triazole group. The triazole group can be formed in a "click" reaction between an azide linker forming group, and an alkyne linker forming group.

In addition, the overall linker can include $C_5$ linear alkyl and amide groups on one or both sides of the triazole moiety.

(III)

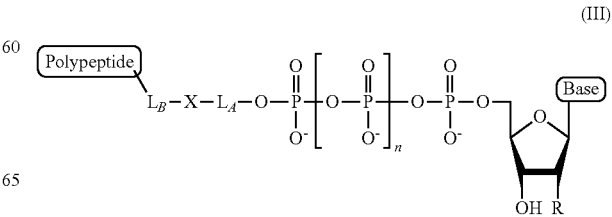

wherein, "Base" is a naturally occurring or non-naturally occurring nucleobase; R is selected from H and OH; n is from 1 to 10; "Polypeptide" is a polypeptide that has an overall charge and comprises at least one helical structure; and "-L$_B$-X-L$_A$-" is a linker wherein L$_A$ and L$_B$ each comprise a covalently bonded chain of 2 to 100 atoms and X is a chemical moiety selected from the group consisting of ester, ether, thioether, amine, amide, imide, carbonate, carbamate, squarate, thiazole, thiazolidine, hydrazone, oxime, triazole, and dihydropyridazine. In some embodiments, L$_A$ and L$_B$ each independently comprises a chemical moiety selected from the group consisting of: linear (C1-C12) alkyl, linear (C1-C12) alkene, linear (C1-C12) alkyne, ester, ether, thioether, amine, amide, imide, carbonate, carbamate, squarate, thiazole, thiazolidine, hydrazone, oxime, triazole, dihydropyridazine, phosphodiester, polyethylene glycol (PEG), and combinations thereof.

Exemplary linker forming groups, X$_A$ and X$_B$, linker precursor moieties, L$_A$ and L$_B$ and the resulting linker that they form, of formula -L$_A$-X-L$_B$-, are shown in Table 1, below.

TABLE 1

| R$_1$--L$_A$--X$_A$* | X$_B$--L$_B$--R$_2$* | R$_1$-L$_A$-X-L$_B$-R$_2$* (or R$_1$-Linker-R$_2$) |
|---|---|---|
| (Va) carboxylic acid | (IVb) H$_2$N—L$_B$—R$_2$ | (IVc) amide |
| (Va) carboxylic acid | (Vb) HO—L$_B$—R$_2$ | (Vc) ester |
| (VIa) R$_1$—L$_A$—SH | (VIb) maleimide-L$_B$—R$_2$ | (VIc) thiosuccinimide |
| (VIIa) R$_1$—L$_A$—SH | (VIIb) Z—L$_B$—R$_2$ wherein, Z is a suitable leaving group, e.g., F, Cl, Br, or I | (VIIc) R$_1$—L$_A$—S—L$_B$—R$_2$ |
| (VIIIa) R$_1$—L$_A$—SH | (VIIIb) HS—L$_B$—R$_2$ | (VIIIc) R$_1$—L$_A$—S—S—L$_B$—R$_2$ |
| (IXa) R$_1$—L$_A$—OH | (IXb) Z—L$_B$—R$_2$ wherein, Z is a suitable leaving group, e.g., F, Cl, Br, or I | (IXc) R$_1$—L$_A$—O—L$_B$—R$_2$ |
| (Xa) R$_1$—L$_A$—NH$_2$ | (Xb) H$_2$N—L$_B$—R$_2$ + dimethyl squarate | (Xc) squaramide |

TABLE 1-continued
| R$_1$—L$_A$—X$_A$* | X$_B$—L$_B$—R$_2$* | R$_1$-L$_A$-X-L$_B$-R$_2$*<br>(or R$_1$-Linker-R$_2$) |
|---|---|---|
| <br>(XIa) | 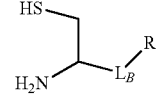<br>(XIb) | 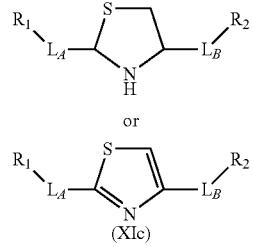<br>or<br>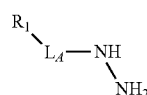<br>(XIc) |
| 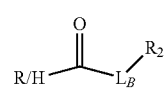<br>(XIIa) | 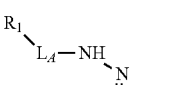<br>(XIIb) | 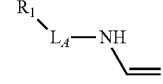<br>(XIIc) |
| 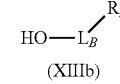<br>(XIIIa) | 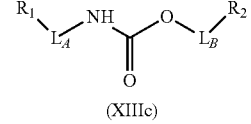<br>(XIIIb) | 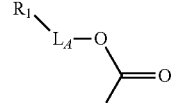<br>(XIIIc) |
| 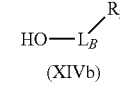<br>wherein, Z is a suitable leaving group, e.g., -OSu, -OBt, or -OAt | 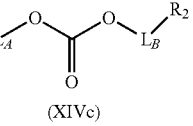<br>(XIVb) | <br>(XIVc) |
| 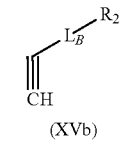<br>(XVa) | 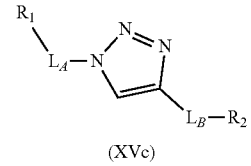<br>(XVb) | <br>(XVc) |
| 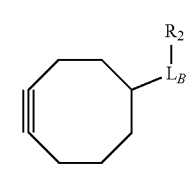<br>(XVIa) | 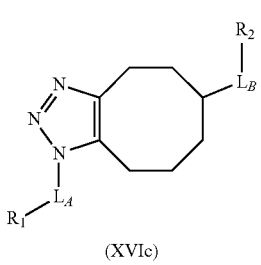<br>(XVIb) | <br>(XVIc) |

TABLE 1-continued

| $R_1$--$L_A$--$X_A$* | $X_B$--$L_B$--$R_2$* | $R_1$-$L_A$-X-$L_B$-$R_2$* (or $R_1$-Linker-$R_2$) |
|---|---|---|
| (XVIIa) — cycloalkene structure with $R_1$-$L_A$- | (XVIIb) — $L_B$-$R_2$ attached to CH$_2$ on 6-membered ring bearing $X_1$, $X_2$ connected to tetrazine ring with $R_3$ | (XVIIc) — fused bicyclic structure with $R_1$-$L_A$-cyclooctane fused to pyridazine with NH, N, $R_3$, connected through $X_1$, $X_2$ to aryl ring bearing $L_B$-$R_2$ |
| | wherein, $X_1$ and $X_2$ are atoms independently selected from C and N; and $R_3$ is a chemical group selected from the group consisting of: H, F, Cl, Br, I, CH$_3$, CF$_3$, NH$_2$, NO$_2$, OH, C(O)OH, C(O)OCH$_3$, C(O)NH$_2$, linear or branched (C$_2$-C$_5$) alkyl, linear or branched (C$_2$-C$_5$) alkenyl, linear or branched (C$_2$-C$_5$) alkynyl, unsubstituted or para-substituted 6-membered aryl ring, and unsubstituted or para-substituted 6-membered heteroaryl ring. | wherein, $X_1$ and $X_2$ are atoms independently selected from C and N; and $R_3$ is a chemical group selected from the group consisting of: H, F, Cl, Br, I, CH$_3$, CF$_3$, NH$_2$, NO$_2$, OH, C(O)OH, C(O)OCH$_3$, C(O)NH$_2$, linear or branched (C$_2$-C$_5$) alkyl, linear or branched (C$_2$-C$_5$) alkenyl, linear or branched (C$_2$-C$_5$) alkynyl, unsubstituted or para-substituted 6-membered aryl ring, and unsubstituted or para-substituted 6-membered heteroaryl ring. |

*$R_1$ and $R_2$ are a polypeptide tag and nucleotide, respectively, or $R_1$ and $R_2$ are a nucleotide and polypeptide tag, respectively Table 1 exemplifies range of linkers and the corresponding reactive linker-forming groups that undergo a reaction that results in the covalent coupling linker. These various linkers and reactions are well-known in the art. The ordinary artisan will be able to identify the reagents needed for these reactions and either synthesize them or obtain them commercially. For example, reagents for conjugating or cross-linking polypeptide (or proteins) to other biomolecules can be used as linker forming groups to prepare the polypeptide-tag-linker-oligophosphate-nucleotide compound structures of the present disclosure. (See e.g., catalog of "crosslinking reagents" available from Thermo Scientific, USA at www.piercenet.com or Sigma-Aldrich, USA at www.sigmaaldrich.com).

Additionally, a wide range of FMOC-protected amino acid residues modified with azide or alkyne groups (or other linker forming groups) that can be used in the automated solid-phase synthesis of polypeptides are commercially available (see e.g., AnaSpec, Fremont, Calif., USA). Similarly, terminal phosphate modified nucleosides and/or reagents for such modification with azide or alkyne groups (or other linker forming groups) are commercially available (see e.g., Jena Bioscience Gmbh, Jena, Germany).

It is contemplated that any of the pairs of linker forming groups of structural formulae (IVa)-(XVIIa) and (IVb)-(XVIIb) can be used in either configuration in preparing a linker in a peptide-tagged nucleotide compounds of the present disclosure (e.g., compound of formula (III)). That is, any of the linker forming groups, $X_A$ and $X_B$ can be used on either the polypeptide tag or the nucleotide, as long as the linker forming groups are paired to provide the linker reaction forming the linker moiety X. Thus, any of the linker forming groups of structural formulae (IVa)-(XVIIa) could be attached to either the polypeptide or the nucleotide, and the conjugate linker forming group of structural formulae (IVb)-(XVIIb) would be attached to the other. Thus, the groups $R_1$ and $R_2$ as depicted in the linkers of form $R_1$-$L_A$-X-$L_B$-$R_2$ in Table 1, can represent either the polypeptide tag and the nucleotide, or the nucleotide and the polypeptide tag, respectively.

Accordingly, in some embodiments, the present disclosure provides polypeptide-tagged nucleotide compounds of formula (III), wherein the compound comprises a compound of formula $R_1$-$L_A$-X-$L_B$-$R_2$, wherein $R_1$ and $R_2$ are the nucleotide and the polypeptide tag, or $R_1$ and $R_2$ are the polypeptide tag and the nucleotide, respectively, and -$L_A$-

X-$L_B$- comprises a chemical moiety selected from the moieties of structural formula (IVc)-(XVIIc) in Table 1.

As described above, the chemical moieties $L_A$ and $L_B$ which make up the linker can each independently comprise chemical moieties including linear ($C_1$-$C_{12}$) alkyl, ester, ether, thioether, amine, amide, imide, carbonate, carbamate, polyethylene glycol (PEG), and combinations thereof. Similar to the linker forming groups $X_A$ and $X_B$, it is contemplated that any of the chemical moieties $L_A$ and $L_B$, which make up the linker, can each independently be used with any of the linker forming groups, and can be used on either the polypeptide tag or the nucleotide. Additionally, it is contemplated that the chemical moieties $L_A$ and $L_B$ can be the same or different. In some embodiments of the polypeptide-tagged nucleotide compounds of formula (III), the $L_A$ and $L_B$ chemical moieties comprise chemical moieties independently selected from the group consisting of moiety structures of formula (XVIIIa)-formula (XVIIId) as in Table 2.

TABLE 2

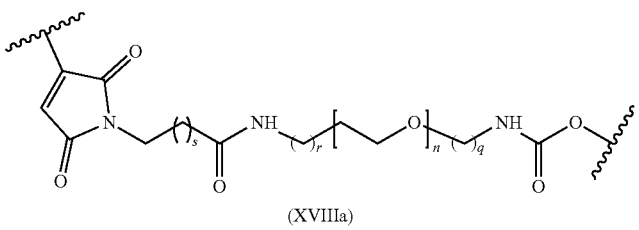

(XVIIIa)

wherein, n = 1 to 50, and q, r, and s each independently = 0, 1, 2, or 3;

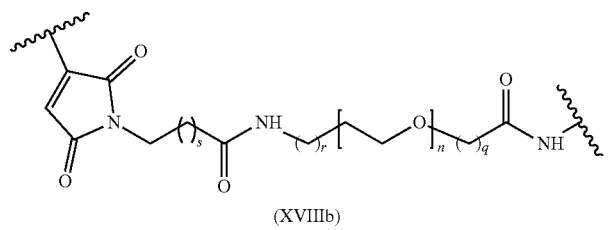

(XVIIIb)

wherein, n = 1 to 50, and q, r, and s each independently = 0, 1, 2, or 3;

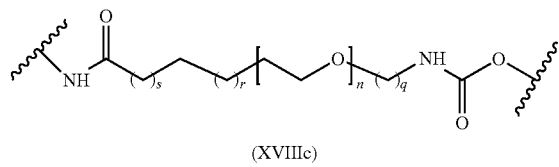

(XVIIIc)

wherein, n = 1 to 50, and q, r, and s each independently = 0, 1, 2, or 3;

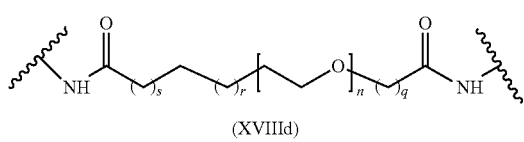

(XVIIId)

wherein, n = 1 to 50, and q, r, and s each independently = 0, 1, 2, or 3.

Although the structural formula of compound (III) depicts the linker as "-$L_B$-X-$L_A$-" as separate moiety covalently coupled to the polypeptide tag, it is contemplated that in some embodiments, this linker can comprise an amino acid residue, which in turn is coupled via a standard peptide bond to the polypeptide tag. Such embodiments, are illustrated in the Examples of the present disclosure, where an amino acid coupled to the polypeptide tag comprises a propargyl (or other alkynyl) group. The propargyl group provides an alkyne "handle" that allows the polypeptide tag to be covalently coupled to a desired nucleotide (or nucleotide analog) via an azide-alkyne or azide-cyclooctyne "click" reaction. This propargyl group acts as a linker forming group (i.e., "$X_B$") and undergoes a linker forming "click" reaction with an azide linker forming group attached to a nucleotide as illustrated in Scheme 2.

Scheme 2

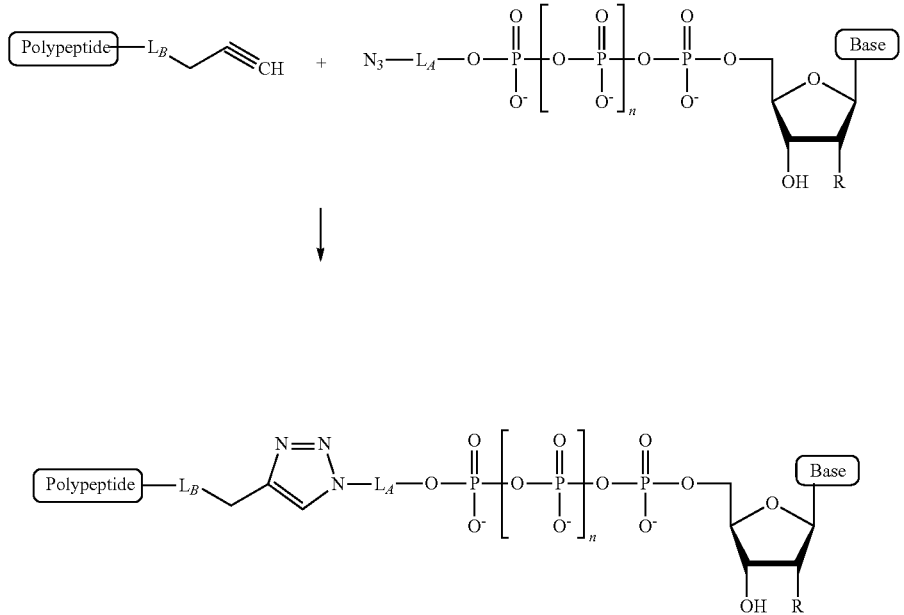

Each of the exemplary polypeptide-tags disclosed herein, (see e.g., Tables 4 and 5, below) can be modified with a propargyl group. Specific possible modifications can include, but are not limited to, a propargyl-glycine ("Pra") amino acid residue at the N-terminus, or a propargyl group covalently linked to the side-chain of the amino acid at the C-terminus (e.g., a propargyl group modification of the side-chain epsilon amine of a C-terminal lysine). It is also possible that a propargyl group can be a modification of an amino acid residue side-chain wherein the amino acid is at an interior portion of the polypeptide sequence (i.e., not at either the N- or C-terminus). Thus, in some embodiments, the polypeptide-tagged nucleotide compound of structural formula (III) (as described above) can further comprise structural formula (XIX) (i.e., wherein X is a triazole group)

(XIX)

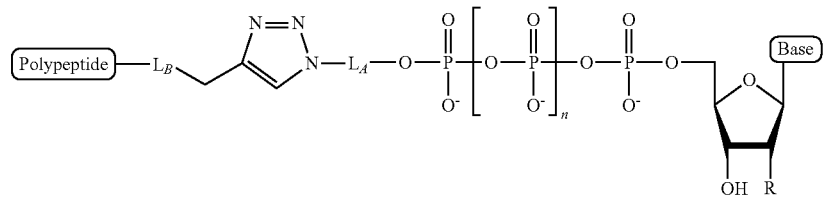

The polypeptide tag can be modified with a propargyl group at the N- or C-terminus or at any other amino acid residues in the polypeptide sequence which are capable of modification. In some embodiments, the propargyl modification can introduced during synthesis of the polypeptide tag by including a propargyl modified amino acid synthesis reagent. Such modified amino acid reagents for use in solid-phase polypeptide synthesis are well known and commercially available. For example, the synthesis of the polypeptide tag can include a step in which an L-propargyl-glycine amino acid is added at its N-terminus. The N-terminal L-propargyl-glycine amino acid residue (also referred to as a "Pra" amino acid) has a propargyl (or 2-propynyl) group at the α-position that can undergo a reaction with an azide-modified nucleotide to form a polypeptide-tagged nucleotide. Thus, in some embodiments, the present disclosure provides a polypeptide-tagged nucleotide compound of structural formula (III), wherein the polypeptide tag (T) is attached to the Linker by the N-terminus of the polypeptide. Such an example using an N-terminal Pra amino acid residue is illustrated in Scheme 3.

Scheme 3

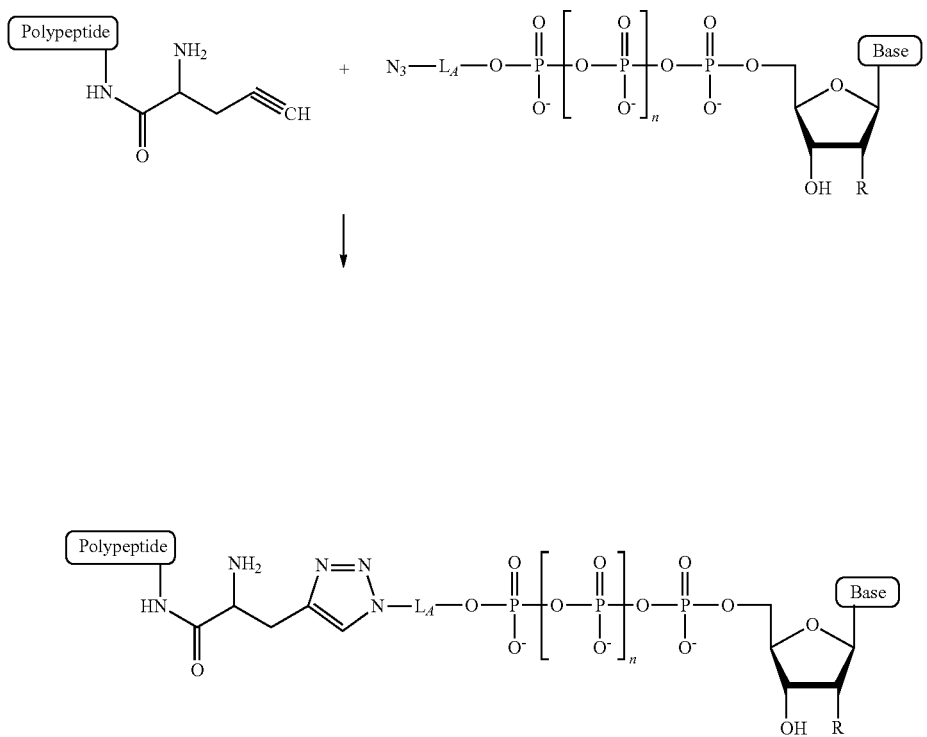

Thus, in some embodiments, the polypeptide-tagged nucleotide compound of structural formula (III) (as described above) can further comprise structural formula (XX) (i.e., wherein $L_B$ comprises a modified glycine amino acid and X is a triazole group)

(XX)

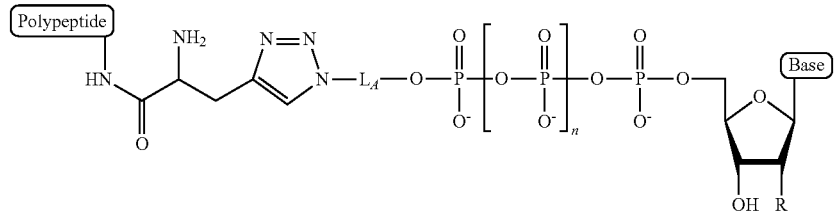

The polypeptide tag can also be synthesized with a propargyl-modified amino acid at the C-terminus or other positions. For example, the reagent $N^2$-[(1,1-Dimethylethoxy)carbonyl]-$N^6$-[(2-propynyloxy)carbonyl]-L-lysine can be used to insert a propargyl-modified lysine residue. In another embodiment, the polypeptide tag can be synthesized via solid phase polypeptide synthesis and then subsequently modified with a propargyl group at a suitable amino acid residue side chain on the polypeptide. For example, a lysine amino acid residue can be added to the C-terminus of the polypeptide tag sequence via standard solid phase polypeptide synthesis. Then subsequent to the polypeptide synthesis the epsilon amine group of the lysine side chain can be modified with a propargyl group using standard conjugation chemistry (e.g., NHS-ester addition). A propargyl-modified lysine can undergo a reaction with an azide-modified nucleotide to form a polypeptide-tagged nucleotide. Such an example using a C-terminal propargyl-modified lysine (i.e., "K(propargyl)) amino acid residue is illustrated in Scheme 4.

Scheme 4

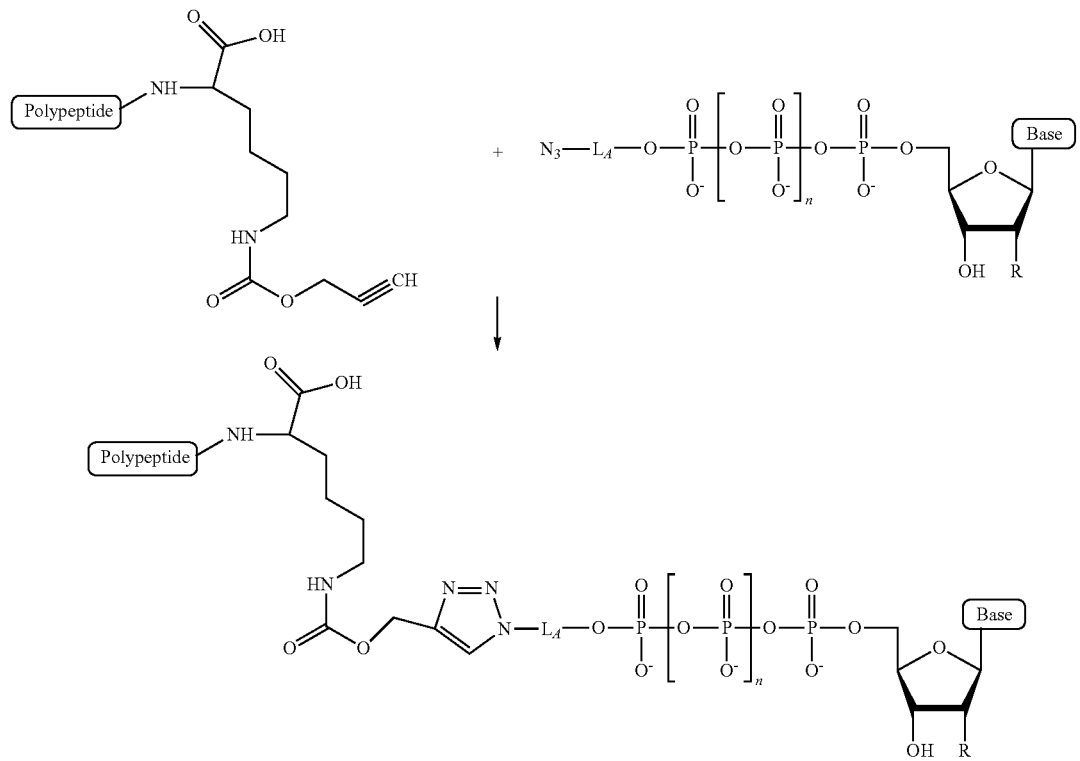

Thus, in some embodiments, the polypeptide-tagged nucleotide compound of structural formula (III) (as described above) can further comprise structural formula (XXI) (i.e., wherein $L_B$ comprises a modified lysine amino acid and X is a triazole group)

(XXI)

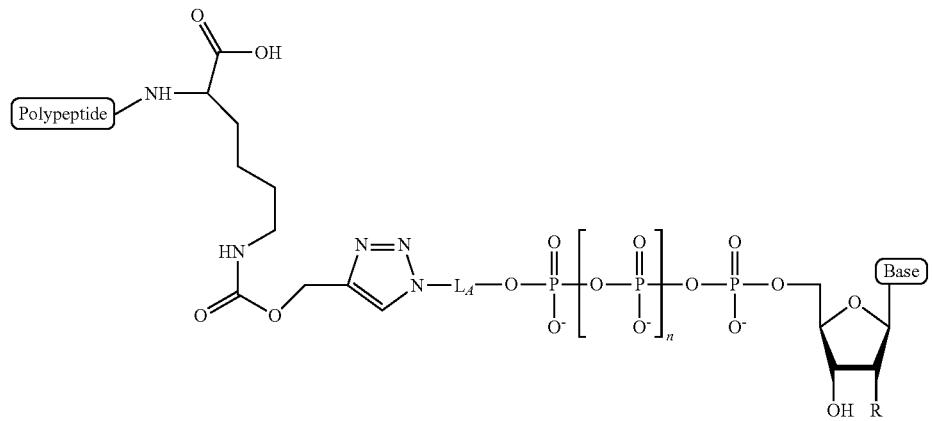

As noted above, it is contemplated that the linker forming groups, $X_A$ and $X_B$ can be used on either the polypeptide tag or the nucleotide, as long as the linker forming groups are paired to provide the linker reaction forming the linker moiety X. For example, the synthesis of the polypeptide tag can include a step in which an azido-modified amino acid (e.g., L-azidobutyl-alanine, azido-lysine, azido-phenylalanine) is added to the sequence (e.g., at its N-terminus) and the terminal phosphate of the nucleotide is modified with an alkyne group. Thus, in some embodiments, the polypeptide tag comprises an azide group and undergoes a "click" reaction with a propargyl (or other alkynyl) group attached to a nucleotide as illustrated in Scheme 5.

Scheme 5

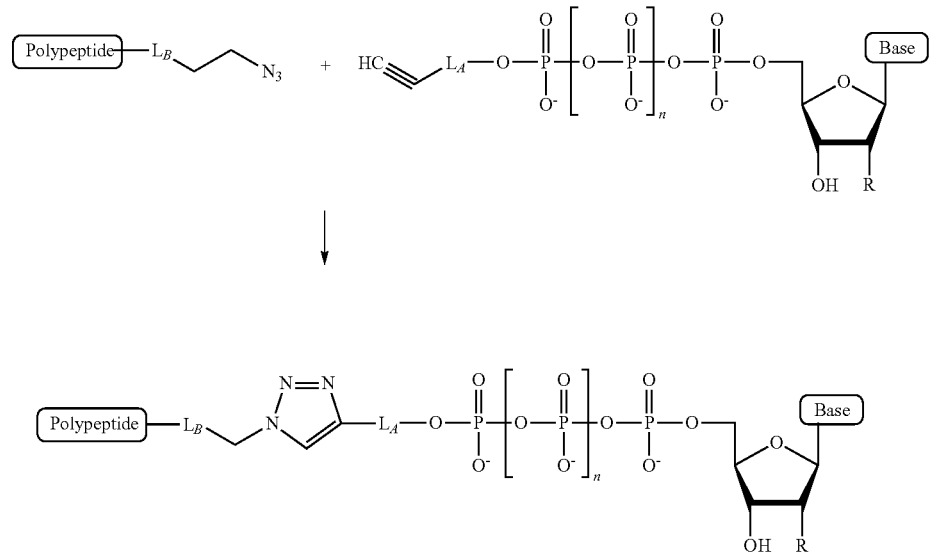

Thus, in some embodiments, the polypeptide-tagged nucleotide compound of structural formula (III) (as described above) can further comprise structural formula (XXII) the triazole group is the opposite orientation relative to the compound of structural formula (XIX).

(XXII)

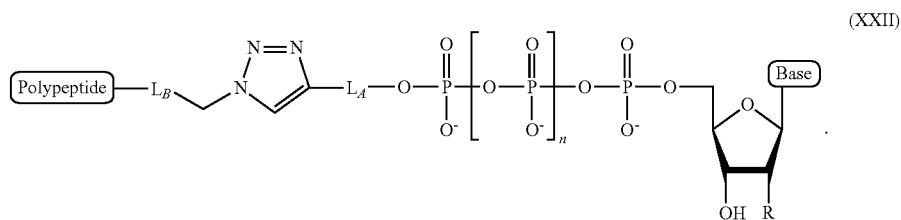

The linkers useful in the polypeptide-tagged nucleotide compounds of the present disclosure, however, are not limited to linkers formed by linker forming groups and having the structure -$L_B$-X-$L_A$- as depicted in the compound of structural formula (III). Although typically it is necessary for two linker forming groups (i.e., $X_A$ and $X_B$) to be present to carry out a linker forming reaction as in Scheme 1, the presence of two precursor linker groups is not. For example, it is contemplated in some embodiments that a linker forming reaction can be carried out wherein one, or both, linker forming groups is attached directly to the polypeptide tag and/or the nucleotide. Thus, the moiety X formed by the reaction between the linker forming groups, $X_A$ and $X_B$ can provide the complete linker. Such an example is illustrated in Scheme 6.

Scheme 6

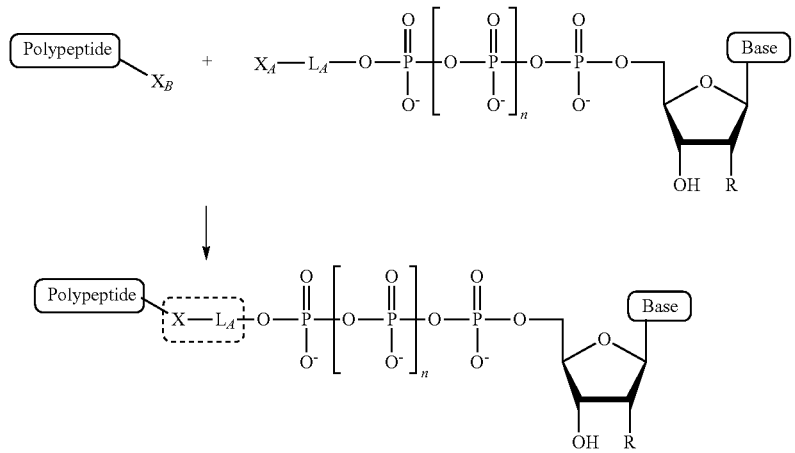

Polypeptide Tags

The polypeptides useful as tags in the polypeptide-tagged nucleotides of the present disclosure generally are polymeric chains of 30 or more amino acids that have an overall charge and at least one helical structure. The helical structures of the polypeptide tags of the present disclosure can provide stronger blocking currents that show less variance when the structure enters and resides in a nanopore. Without intending to be limited by any proposed theory or mechanism, it is believed that polypeptides having helical structures, such as α-helix loops, of 16 amino acids or longer (e.g., from 16 to 80 amino acids), can fit in the pore of a nanopore better so as to provide stronger current blocking currents and longer dwell times than polypeptides having linear or random coil structures. Accordingly, the present disclosure provides polypeptide tags with amino acid sequences that have a range of lengths, helical structures, and overall charges.

In some embodiments of the polypeptide tags, the polypeptide length is at least 10 amino acids, at least 16 amino acids, at least 20 amino acids, at least 25 amino acids, at least 30 amino acids, at least 40 amino acids, at least 50 amino acids, at least 60 amino acids, at least 70 amino acids, at least 80 amino acids, or even more amino acids. In some embodiments, the length of the polypeptide is from 10 to 100 amino acids, from 16 to 90 amino acids, from 30 to 90 amino acids, from 40 to 80 amino acids, or from 50 to 70 amino acids.

The polypeptide tags of the present disclosure are not restricted to the 20 genetically encoded amino acids. In addition to the genetically encoded amino acids, the polypeptides described herein may comprise, either in whole or in part, other synthetic or naturally-occurring non-encoded amino acids including, but not limited to: the D-stereisomers of the genetically-encoded L-amino acids; the 3-substituted amino acid isomers (e.g., β-alanine) of the genetically encoded α-amino acids; 2,3-diaminopropionic acid (Dpr); α-aminoisobutyric acid (Aib); ε-aminohexanoic acid (Aha); δ-aminovaleric acid (Ava); N-methylglycine or sarcosine (MeGly or Sar); ornithine (Orn); citrulline (Cit); t-butylalanine (Bua); t-butylglycine (Bug); N-methylisoleucine (MeIle); phenylglycine (Phg); cyclohexylalanine (Cha); norleucine (Nle); naphthylalanine (Nal); 2-chlorophenylalanine (Ocf); 3-chlorophenylalanine (Mcf); 4-chlorophenylalanine (Pcf); 2-fluorophenylalanine (Off); 3-fluorophenylalanine (Mff); 4-fluorophenylalanine (Pff); 2-bromophenylalanine (Obf); 3-bromophenylalanine (Mbf); 4-bromophenylalanine (Pbf); 2-methylphenylalanine (Omf); 3-methylphenylalanine (Mmf); 4-methylphenylalanine (Pmf); 2-nitrophenylalanine (Onf); 3-nitrophenylalanine (Mnf); 4-nitrophenylalanine (Pnf); 2-cyanophenylalanine (Ocf); 3-cyanophenylalanine (Mcf); 4-cyanophenylalanine (Pcf); 2-trifluoromethylphenylalanine (Otf); 3-trifluoromethylphenylalanine (Mtf); 4-trifluoromethylphenylalanine (Ptf); 4-aminophenylalanine (Paf); 4-iodophenylalanine (Pif); 4-aminomethylphenylalanine (Pamf); 2,4-dichlorophenylalanine (Opef); 3,4-dichlorophenylalanine (Mpcf); 2,4-difluorophenylalanine (Opff); 3,4-difluorophenylalanine (Mpff); pyrid-2-ylalanine (2pAla); pyrid-3-ylalanine (3pAla); pyrid-4-ylalanine (4pAla); naphth-1-ylalanine (1nAla); naphth-2-ylalanine (2nAla); thiazolylalanine (taAla); benzothienylalanine (bAla); thienylalanine (tAla); furylalanine (fAla); homophenylalanine (hPhe); homotyrosine (hTyr); homotryptophan (hTrp); pentafluorophenylalanine (5ff); styrylkalanine (sAla); authrylalanine (aAla); 3,3-diphenylalanine (Dfa); 3-amino-5-phenypentanoic acid (Afp); penicillamine (Pen); 1,2,3,4-tetrahydroisoquinoline-3-carboxylic acid (Tic); β-2-thienylalanine (Thi); methionine sulfoxide (Mso); N(w)-nitroarginine (nArg); homolysine (hLys); phosphonomethylphenylalanine (pmPhe); phosphoserine (pSer); phosphothreonine (pThr); homoaspartic acid (hAsp); homoglutanic acid (hGlu); 1-aminocyclopent-(2 or 3)-ene-4 carboxylic acid; pipecolic acid (PA), azetidine-3-carboxylic acid (ACA); 1-aminocyclopentane-3-carboxylic acid; allylglycine (aOly); propargylglycine (Pra); homoalanine (hAla); norvaline (nVal); homoleucine (hLeu), homovaline (hVal); homoisolencine (hIle); homoarginine (hArg); N-acetyl lysine (AcLys); 2,4-diaminobutyric acid (Dbu); 2,3-diaminobutyric acid (Dab); N-methylvaline (Me-Val); homocysteine (hCys); homoserine (hSer); hydroxyproline (Hyp); and homoproline (hPro). Additional non-encoded amino acids useful in the polypeptide tags described herein will be apparent to those of skill in the art (see, e.g., the various amino acids provided in Fasman, 1989, CRC Practical Handbook of Biochemistry and Molecular Biology, CRC Press, Boca Raton, Fla., at pp. 3-70 and the references cited therein, all of which are incorporated by reference). These amino acids may be in either the L- or D-configuration.

Those of skill in the art will recognize that the polypeptide tags of the present disclosure may also comprise amino acids bearing side-chain protecting group. Examples of such amino acids with protected side-chains include but are not limited to (protecting groups listed in parentheses): Arg(tos), Cys(methylbenzyl), Cys (nitropyridinesulfenyl), Glu(δ-benzylester), Gln(xanthyl), Asn(N-δ-xanthyl), His(bom), His (benzyl), His(tos), Lys(fmoc), Lys(tos), Ser(O-benzyl), Thr (O-benzyl) and Tyr(O-benzyl).

The polypeptide helical structure of the polypeptide tags of the present disclosure may comprise all of the amino acid residues of the polypeptide or some sub-portion(s) of the polypeptide. Accordingly, in some embodiments of the polypeptide tags, the polypeptide helical structure comprises is at least 10 amino acids, at least 16 amino acids, at least 20 amino acids, at least 25 amino acids, at least 30 amino acids, at least 40 amino acids, at least 50 amino acids, or at least 60 amino acids.

The alpha helix (α-helix) is a common and well-characterized helical structure useful in the polypeptide-tagged nucleotides of the present disclosure. The α-helix has a right handed spiral conformation in which every backbone N—H group donates a hydrogen bond to the backbone C=O group of the amino acid four residues earlier. Among the types of polypeptide structures, the α-helix is the most prevalent and easily predicted based on amino acid sequence. Principles for the design of polypeptides with α-helical structures are well-studied and established in the art (see e.g., Garner & Harding, "Design and synthesis of α-helical peptides and mimetics," Org. Biomol. Chem., 2007, 5, 3577-3585; and Doig, "Stability and Design of α-Helical Peptides," Progress in Molecular Biology and Translational Science, Vol. 83, pp. 1-52, Elsevier 2008). These general principles can be used to design polypeptide tags having helical structure that are useful in the polypeptide-tagged nucleotide compounds of the present disclosure.

Different amino-acid sequences have different propensities for forming α-helical structure. Methionine, alanine, leucine, glutamic acid, and lysine ("MALEK" in the amino-acid 1-letter codes) all have especially high helix-forming propensities, whereas proline and glycine have poor helix-forming propensities. Proline is an amino acid residue that disrupts an amino acid sequence from forming a helical structure, such as an α-helix. Proline, however, can act as the first residue of a helix. Glycine also tends to disrupt helical structures, it is believed due the entropic unfavorability of its high conformational flexibility adopting a relatively constrained helical structure.

For example, the propensity of an amino acid to form an α-helix structure can be estimated based on the difference in free energy, estimated in kcal/mol per residue when the amino acid is in an α-helix, relative to the amino acid alanine, which is arbitrarily set as zero. The α-helix forming propensity of amino acid residues have been estimated based on free energy differences (see e.g., Pace, et al. (1998), "A Helix Propensity Scale Based on Experimental Studies of Peptides and Proteins," Biophysical Journal 75: 422-427; doi:10.1016/s0006-3495(98)77529-0.) As shown in Table 3 below for the 20 genetically encoded L-amino acids, the amino acid residues Ala, Arg, Leu, Met, Lys, Gln, and Glu, exhibit relatively high propensity to form a helical structure (more positive free energies have lower helix forming propensity). These relative propensity values can vary, however, depending on the neighboring amino acid residues.

TABLE 3

| AMINO ACID | AMINO ACID | HELICAL PROPENSITY (KCAL/MOL) |
|---|---|---|
| ALA | A | 0 |
| ARG | R | 0.21 |
| LEU | L | 0.21 |
| MET | M | 0.24 |
| LYS | K | 0.26 |
| GLN | Q | 0.39 |
| GLU | E | 0.40 |
| ILE | I | 0.41 |
| TRP | W | 0.49 |
| SER | S | 0.50 |
| TYR | Y | 0.53 |
| PHE | F | 0.54 |
| HIS | H | 0.61 |
| VAL | V | 0.61 |
| ASN | N | 0.65 |
| THR | T | 0.66 |
| CYS | C | 0.68 |
| ASP | D | 0.69 |
| GLY | G | 1.00 |
| PRO | P | 3.16 |

In some embodiments of the present disclosure, the polypeptide tag of the polypeptide-tagged nucleotides comprises a helical structure that comprises an α-helix. In some embodiments, the α-helix comprises at least two repeats of a sequence motif comprising at least three amino acids. Optionally, the sequence motif comprising at least three amino acids is a homopolymer, and further optionally, the homopolymeric sequence motif comprising at least three amino acids comprises the sequence AAA.

In some embodiments, the α-helix comprises at least two repeats of a sequence motif that consists of four amino acids. Optionally, the four amino acid sequence motif comprises at least two A residues. In some embodiments, the α-helix comprises at least two repeats of a sequence motif that consists of eight amino acids. In some embodiments, the α-helix comprises a sequence motif comprising a four amino acid sequence comprising at three A residues. In some embodiments, the four amino acid sequence motif comprises three alanine residues and a charged amino acid residue. Optionally, the four amino acid sequence motif comprises a motif selected from the group of motifs consisting of: EAAA, AEAA, AAEA, AAAE, DAAA, ADAA, AADA, AAAD, RAAA, ARAA, AARA, AAAR, KAAA, AKAA, AAKA, and AAAK. In some embodiments, the α-helix comprises a sequence motif comprising a four amino acid sequence motif, wherein the motif comprises at least two A residues, a charged amino acid residue, and an amino acid with a side-chain that provides steric hindrance. Optionally, the amino acid with a side-chain that provides steric hindrance selected from the group consisting of F, H, I, L, M, T, W, and Y.

In some embodiments of the polypeptide tag comprising an α-helix, the α-helix comprises at least two repeats of a sequence motif, wherein the repeats are not interrupted by an amino acid residue that has a low propensity for α-helix formation, such as amino acid residues with a helical propensity greater than 0.50, or greater than 0.60, or at least 1.00 (as listed above in Table 3).

In some embodiments of the polypeptide tag comprising an α-helix, the α-helix comprises at least two repeats of a sequence motif, wherein the repeats are not interrupted by an amino acid residue that is non-helix-forming (or helix disrupters). Such non-helix forming residues can include, but are not limited to, P and G.

In some embodiments of the polypeptide tag comprising an α-helix, the α-helix comprises at least two repeats of a sequence motif, wherein the repeats are not interrupted by an amino acid residue selected from the group consisting of C, D, F, G, H, N, P, T, V, and Y. In some embodiments the α-helix comprises at least two repeats of a sequence motif, wherein the repeats are not interrupted by an amino acid residue selected from the group consisting of C, D, G, H, N, P, T, and V. In some embodiments the α-helix comprises at least two repeats of a sequence motif, wherein the repeats are not interrupted by an amino acid residue selected from the group consisting of G, and P.

In some embodiments of the polypeptide tag of the present disclosure, the polypeptide comprises an α-helix, wherein the length of the α-helix is at least 10 amino acids, at least 16 amino acids, at least 20 amino acids, at least 25 amino acids, at least 30 amino acids, or at least 40 amino acids. In some embodiments, at least 50% of the amino acid residues of the α-helix are A residues. In some embodiments at least 75% of the amino acid residues of the α-helix are A residues. Thus, in some embodiments, the polypeptide tag comprises an α-helix, wherein the length of the α-helix is at least 16 amino acids and the α-helix comprises at least 6 A residues (i.e., 50%). In some embodiments, the polypeptide tag comprises an α-helix, wherein the length of the α-helix is at least 40 amino acids and the α-helix comprises at least 30 A residues (i.e., 75% alanine residues).

The capture and detection of a tagged nucleotide by a nanopore can be facilitated by the charge of the tag molecule. Generally, when a nanopore detection system is set-up under an alternating current (AC) or direct current (DC) potential with the cis side of the pore (i.e., reservoir side with nucleotides and polymerase) having a negatively-charged electrode and the trans side having a positively-charged electrode, it is preferred that the tag of the tagged nucleotide has a negative charge. Under such conditions, the capture and detection of the negatively-charged tag can be facilitated by the electromotive force provided by the trans side positive electrode. Alternatively, a positively-charged tag generally would be preferred under conditions wherein the trans side of the nanopore system comprises a negative electrode.

The present disclosure provides polypeptide-tagged nucleotides wherein the polypeptide has 30 or more amino acids and an overall charge. The overall charge is that net charge of the whole polypeptide based on summing the charge of each of the amino acid side chains that make up the polypeptide. Because a large variety of charged amino acid residues are available that can be incorporated into a polypeptide sequence, the overall charge of a polypeptide tag of the present disclosure can be easily adjusted (or tuned) over a wide range to allow for a wide range of possible nanopore detection characteristics.

In some embodiments, the present disclosure provides polypeptide-tagged nucleotides, wherein the overall charge of the polypeptide is negative. In some embodiments, the overall charge of the polypeptide is between about −10 and −30. In the embodiments where the overall charge of the polypeptide is negative, the polypeptide sequence can comprise one or more negatively charged amino acid residues, wherein the negatively charged residues can be the same or different. For example, in the case of polypeptide tag having an overall charge of −10, the polypeptide sequence would need to comprise at least 10 negatively charged residues. In some embodiments, the negatively charged residues are selected from the group consisting of glutamic acid, aspartic acid, gamma-carboxy glutamic acid, homo-glutamic acid, cysteic acid, phospho-serine, phospho-threonine, phospho-tyrosine, and combinations thereof.

Alternatively, in some embodiments of the polypeptide-tagged nucleotides, the overall charge of the polypeptide is positive, and optionally has an overall charge of between about +10 and +30. In such embodiments, the polypeptide sequence can comprise one or more positively charged amino acid residues, optionally selected from the group consisting of: arginine, lysine, and histidine.

It is contemplated that in some embodiments the overall charge of the polypeptide tag can be distributed equally over the length of the polypeptide tag. In some embodiments, however, the overall charge of the polypeptide tags of the present disclosure can be distributed unequally over the length of the polypeptide sequence. Such unequal charge distribution can provide the tag with further distinguishing characteristics under nanopore detection conditions, e.g., either AC or DC potential. Accordingly, in some embodiments the present disclosure provides a polypeptide-tagged nucleotide wherein the 25% of the amino acid residues located at the end of the polypeptide tag distal (i.e., further) from the linker have an net charge absolute value greater than the net charge absolute value of the 25% of the amino acid residues located at the end of the polypeptide proximal (i.e., nearer) to the linker. That is, if overall charge is negative, the 25% of the amino acid residues distal from the linker would be more negatively charged than the 25% of the amino acid residues proximal to the linker.

In some embodiments of polypeptide-tagged nucleotides with a peptide tag having an overall charge unequally distributed, at least the three amino acid residues of the polypeptide at the terminus distal from the linker are negatively charged residues. In some embodiments, at least the five amino acid residues of the polypeptide at the terminus distal from the linker are negatively charged residues. In some embodiments, there are at least six, seven, eight, nine, or ten, or more negatively charged residues at the terminus distal from the linker. In some embodiments, the at least three, four, five, six, or more, negatively charged amino acid residues at the terminus are the same amino acid, e.g., EEEEEE, or DDDDD. In some embodiments, the at least three, four, five, six, or more, negatively charged amino acid residues at the terminus are a mix of different negatively charged amino acids, e.g., EEEDDD, or DEDED, or EEDEE.

Utilizing the knowledge in the art regarding amino acid residues, the charge, length, volume, and mass characteristics, and their known propensities to form certain types of structures when polymerized in polypeptide sequences (e.g., α-helix-forming propensity), and following the present disclosure regarding the use of tagged nucleotides in nanopore detection it is possible to design a variety of polypeptide tags that can provide a range of characteristics suitable for nanopore detection. Table 4 shows exemplary polypeptide tags that can be used in polypeptide-tagged nucleotides of the present disclosure.

Thus, in some embodiments, the present disclosure provides a polypeptide-tagged nucleotide compound wherein the polypeptide tag (T) comprises a polypeptide tag sequence of Table 4. In some embodiments, the present disclosure provides a polypeptide-tagged nucleotide compound of any one of structural formulas (I), (II), (III), (XIX), (XX), (XXI), or (XXII), wherein the polypeptide tag comprises a polypeptide tag sequence of Table 4.

TABLE 4

(Seq. ID. Nos 1-14)

| Polypeptide tag | # amino acids | Overall charge | Structural and Charge Features |
|---|---|---|---|
| (EAAA)$_{16}$-E$_5$ | 69 | −21 | α-helical peptide; negatively charged; long length |
| (EAAA)$_{13}$-E$_5$ | 57 | −18 | α-helical peptide; negatively charged; medium length |
| (EAAA)$_{10}$-E$_5$ | 45 | −15 | α-helical peptide; negatively charged; short length |
| (EAAA)$_{16}$-Gla$_4$-E | 69 | −25 | pore entry enhancing peptide; has 4 C-terminal Gla (gamma carboxy glutamic acid) residues |
| Biotin-(UE)$_{25}$ | 51 | −25 | random coil; N-terminal biotin group |
| (EAAA)$_8$-P-(EAAA)$_8$-E$_5$ | 70 | −21 | α-helical peptide; 1 helix breaker; negatively charged; long length |
| (EAAA)$_4$-P-(EAAA)$_4$-P-(EAAA)$_4$-P-(EAAA)$_4$-E$_5$ | 70 | −21 | α-helical peptide; 3 helix breakers; negatively charged; long length |
| (EAAAKAAA)$_4$-(EAAA)$_8$-E$_5$ | 69 | −13 | α-helical peptide; reduced negative net charges; long length |
| (EAAAKAAA)$_8$-E$_5$ | 69 | −5 | α-helical peptide; more reduced negative net charges; long length |
| (E-P$_9$)$_5$-E$_5$ | 55 | −10 | oligoproline helix (long); interrupted by Glu; less negative charges |
| (E-P$_3$)$_{16}$-E$_5$ | 69 | −21 | oligoproline helix (short); interrupted by Glu; more negative charges |
| P$_{45}$-E$_5$ | 50 | −5 | oligoproline helix; no Glu interruption; negative charges low |
| (RAAA)$_{16}$-R$_5$ | 69 | +21 | α-helical peptide; positively charged |
| (EATA)$_{16}$-E$_5$ | 69 | −21 | α-helical peptide; sterically demanding side chains; negatively charged; long length |

Abbreviations
"U" = beta-alanine
"Gla" = gamma-carboxy glutamic acid

The exemplary polypeptide tags shown in Table 4 comprise natural and/or unnatural amino acid monomers and can be prepared by standard solid-phase polypeptide synthesis methods. Additionally, these polypeptide tags (and virtually any other polypeptide sequence of up to 80 amino acids) are commercially available from custom peptide vendors such Peptide 2.0 (Chantilly, Va., USA) or GenScript (Piscataway, N.J., USA).

Standard synthetic methods can be used in preparing the polypeptide-tagged nucleotide compounds of the present disclosure (e.g., compounds of structural formulas (I), (II), (III)). The standard azido-alkyne click reaction is described above (e.g., compounds of (XIX), (XX), (XXI), or (XXII)) and in the Examples. Tables 1 and 2 illustrate a range of linkers and linker forming group reactions that can be used in preparing the peptide-tagged nucleotides of the present disclosure. Any of the linker forming groups of structural formulas (IVa)-(XVIIa) shown in Table 1 can be attached to either the polypeptide or the terminal phosphate of a nucleotide, and the conjugate linker forming group of structural formulae (IVb)-(XVIIb) would be attached to the other. The resulting polypeptide-linker-oligophosphate-nucleotide structures are exemplified in Table 1 by structural formulae (IVc)-(XVIIc), and include the dihydropyrazidine group structure (XVIII) that results from the click reaction of trans-cyclooctene (XVIIa) and tetrazine (XVIIb) linker forming groups.

Accordingly, the present disclosure provides a method of preparing a tagged nucleotide comprising: (a) providing (i) a nucleotide with from 3 to 12 phosphates attached to its 5'-position, wherein the terminal phosphate is coupled to a first linker forming group (e.g., X$_A$ or X$_B$); and (ii) a polypeptide tag, wherein the polypeptide tag comprises at least one helical structure, has an overall charge, and is coupled to a second linker forming group (e.g., X$_B$ or X$_A$) that is capable of reacting with the first linker forming group to form a linker (e.g., —X—); and (b) reacting the first linker forming group with the second linker forming group to link the nucleotide to the polypeptide tag. First and second linker forming groups that are capable of reacting to form a linker are exemplified in Table 1 above. Thus, in some embodiments of the method, the first linker forming group is selected from the compounds of structural formulas (IVa)-(XVIIa) and the second linker forming group is the corresponding reactive compound of structural formulas (IVb)-(XVIIb); or alternatively, the first linker forming group can selected from the compounds of structural formulas (IVb)-(XVIIb) and the second linker forming group is the corresponding reactive compound of structural formulas (IVa)-(XVIIa).

In some embodiments, the disclosure provides method of preparing a polypeptide-tagged nucleotide compound of structural formula (II)

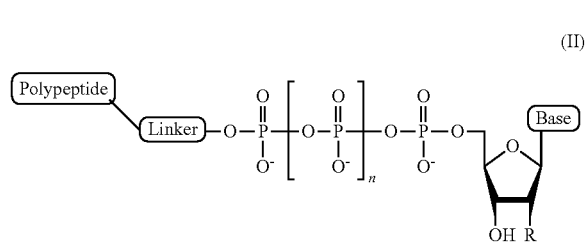

(II)

wherein, Base is selected from adenosine, cytidine, guanosine, thymidine, and uridine; R is selected from H and OH; n is from 1 to 4; Linker is a linker comprising a covalently bonded chain of 2 to 100 atoms; and Polypeptide is a polypeptide tag comprising an overall charge and at least one helical structure; and the method comprises the steps of: (a) providing (i) a nucleotide with from 3 to 12 phosphates attached to its 5'-position, wherein the terminal phosphate is coupled to a first linker forming group; and (ii) a polypeptide tag, wherein the polypeptide tag comprises at least one helical structure, has an overall charge, and is coupled to a second linker forming group, that is capable of reacting with the first linker forming group to form a linker;
wherein
(1) the first linker forming group is selected from the compounds of structural formulas (IVa)-(XVIIa) and the second linker forming group is the corresponding reactive compound of structural formulas (IVb)-(XVIIb); or
(2) the first linker forming group is selected from the compounds of structural formulas (IVb)-(XVIIb) and the second linker forming group is the corresponding reactive compound of structural formulas (IVa)-(XVIIa);
and
(b) reacting the first linker forming group with the second linker forming group, thereby forming a covalent linkage between the nucleotide to the polypeptide tag.

In some embodiments of the methods of preparing the polypeptide-tagged nucleotide, the first linker forming group attached to the terminal phosphate is an azide group and the second linker forming group attached the polypeptide tag is an alkyne. In other embodiments, the first linker forming group attached to the terminal phosphate is an alkyne group and the second linker forming group attached the polypeptide tag is an azide.

In some embodiments of the methods of preparing the polypeptide-tagged nucleotide, the first linker forming group attached to the terminal phosphate is a tetrazine and the second linker forming group attached the polypeptide tag is a trans-cyclooctene. In other embodiments, the first linker forming group attached to the terminal phosphate is a trans-cyclooctene and the second linker forming group attached the polypeptide tag is a tetrazine.

Use of Polypeptide-Tagged Nucleotides in Nanopore Sequencing

The polypeptide-tagged nucleotide compounds of the present disclosure can be used in the known nanopore sequencing methods wherein nanopore detects the presence of a tag attached to a complementary nucleotide as it is incorporated (or after it is incorporated and released) by a strand-extending enzyme (e.g., polymerase, ligase) located proximal to the nanopore and which is extending a primer complementary of a target nucleic acid sequence. General methods, materials, devices, and systems for carrying out nanopore sequencing using tagged nucleotides are described in US Pat. Publ. Nos. 2013/0244340 A1, 2013/0264207 A1, 2014/0134616 A1, 2015/0119259 A1, and U.S. Ser. No. 14/666,124, filed Mar. 23, 2015, each of which is hereby incorporated by reference herein. The polypeptide-tagged nucleotides of the present disclosure can be employed in these general methods for using tagged-nucleotides for nanopore sequencing of nucleic acids.

Thus, in one embodiment, the present disclosure provides a method for determining the sequence of a nucleic acid comprising: (a) providing a nanopore sequencing composition comprising: a membrane, an electrode on the cis side and the trans side of the membrane, a nanopore with its pore extending through the membrane, an electrolyte solution in contact with both electrodes, an active polymerase situated adjacent to the nanopore, and a primer strand complexed with the polymerase; (b) contacting the nanopore sequencing composition with (i) a strand of the nucleic acid; and (ii) a set of tagged nucleotides each with a different tag, wherein each different tag causes a different blocking current level across the electrodes when it is situated in the nanopore, and the set comprises at least one compound of structural formula (I)

N-P-L-T (I)

wherein, N is a nucleoside; P is an oligophosphate covalently attached to a 5'-O group of the nucleoside, wherein the oligophosphate comprises 3 to 12 phosphate groups; L is a linker covalently attached to a terminal phosphate group of the oligophosphate; and T is a polypeptide tag covalently attached to the linker, wherein the polypeptide has an overall charge and comprises at least one helical structure; and (d) detecting current levels across the electrodes over time and correlating to each of the different tagged nucleotides incorporated by the polymerase which are complimentary to the nucleic acid sequence, and thereby determining the nucleic acid sequence.

In some embodiments of the method for determining the sequence of a nucleic acid, the set of tagged nucleotides each with a different tag, comprises at least one compound that comprises a structure of formula (II):

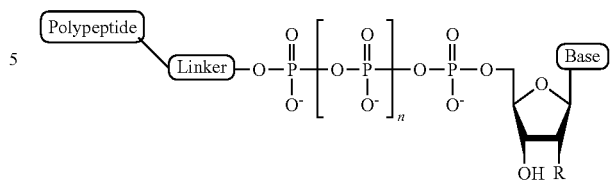

wherein, "Base" is a naturally occurring or non-naturally occurring nucleobase; R is selected from H and OH; n is from 1 to 10; "Linker" is a linker comprising a covalently bonded chain of 2 to 100 atoms; and "Polypeptide" is a polypeptide tag that has an overall charge and comprises at least one helical structure.

When used in the methods for determining the sequence of a nucleic acid the polypeptide-tagged nucleotide compounds comprising structures of formula (I) or (II) can include any of the ranges of compound embodiments disclosed elsewhere herein. For example, the nucleoside (N) of formula (I) can be any nucleoside capable of being incorporated by a strand-extending enzyme, such as a polymerase, when the nucleoside is covalently coupled to an oligophosphate (P), such as a triphosphate; and the nucleoside can comprise a naturally occurring or non-naturally occurring nucleobase, and a naturally occurring or non-naturally occurring sugar moiety, such as a ribose or deoxyribose group.

Sets of Tagged Nucleotides

As described elsewhere herein, methods for determining the sequence of a nucleic acid using nanopore detection generally require a set of tagged nucleotides each comprising a different tag associated with a nucleotide that is desired to be detected. In standard embodiments for sequencing DNA strands, the method requires a set of at least the four standard deoxy-nucleotides dA, dC, dG, and dT, wherein each nucleotide has an attached tag capable of being detected by a nanopore upon the nucleotide being incorporated by a proximal strand extending enzyme, and furthermore wherein the nanopore detection of the tag is distinguishable from the nanopore detection of each of the other three tags, thereby allowing identification of the specific nucleotide associated with the tag via nanopore detection. Generally, the each of the different tagged nucleotides in the set is distinguished by the distinctive nanopore detection characteristics the tag induces when it is situated in the nanopore during the incorporation event catalyzed by the proximal strand-extending enzyme. Among the nanopore detection characteristics, alone or in combination, that can be used to distinguish the tagged nucleotides include the blocking current level across the electrodes of the nanopore detection system (under either DC or AC potential), and the dwell time of the blocking current. Accordingly, in some embodiments, the present disclosure provides a set of tagged nucleotides each with a different tag, wherein each different tag causes a different blocking current level across the electrodes and/or a different dwell time when it is situated in the nanopore, and the set comprises at least one compound of structural formula (I)

N-P-L-T (I)

wherein, N is a nucleoside; P is an oligophosphate covalently attached to a 5'-O group of the nucleoside, wherein the oligophosphate comprises 3 to 12 phosphate groups; L is a linker covalently attached to a terminal phosphate group of the oligophosphate; and T is a polypeptide tag covalently attached to the linker, wherein the polypeptide has an overall charge and comprises at least one helical structure.

In some embodiments of the set of tagged nucleotides each with a different tag, the set comprises at least one compound that comprises a structure of formula (II):

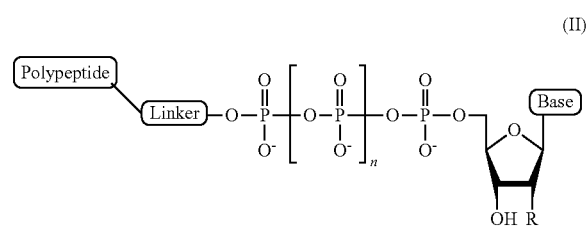

(II)

wherein, "Base" is a naturally occurring or non-naturally occurring nucleobase; R is selected from H and OH; n is from 1 to 10; "Linker" is a linker comprising a covalently bonded chain of 2 to 100 atoms; and "Polypeptide" is a polypeptide tag that has an overall charge and comprises at least one helical structure.

It is contemplated that the polypeptide-tagged nucleotides of the present disclosure may be used in sets of tagged nucleotides having tags that are not polypeptides. For example, in some embodiments, the set of tagged nucleotides can comprise a polypeptide-tagged nucleotide of structural formula (I) or (II) and the other tagged nucleotides in the set can comprise non-polypeptide tags, wherein the non-polypeptide tag is a nanopore detectable compound or polymer, such as an oligonucleotide, a polyethylene glycol polymer, a carbohydrate, or a dye compound. Other tagged nucleotide sets, such as sets of oligonucleotide-tagged nucleotides, are known in the art. (See e.g., US Pat. Publ. Nos. 2013/0244340 A1, 2013/0264207 A1, 2014/0134616 A1, 2015/0119259 A1, and U.S. Ser. No. 14/666,124, filed Mar. 23, 2015, each of which is hereby incorporated by reference herein.) In some embodiments, the set of tagged nucleotides the set comprises at least two, at least three, or at least four polypeptide-tagged nucleotide compounds of structural formula (I) or structural formula (II), wherein each of the different peptide tags of the at least two, at least three, or at least four of the polypeptide-tagged nucleotide compounds in the set is has nanopore detection characteristics that are distinguishable from the others in the set. Methods and techniques for determining the nanopore detection characteristics, such as blocking current and/or dwell time, are known in the art. (See e.g., US Pat. Publ. Nos. 2013/0244340 A1, 2013/0264207 A1, 2014/0134616 A1, 2015/0119259 A1, and U.S. Ser. No. 14/666,124, filed Mar. 23, 2015, each of which is hereby incorporated by reference herein) and include methods such as nanopore static capture experiments under DC or AC voltage potentials using a nanopore array microchip, as described in the Examples herein.

Accordingly, in some embodiments, the present disclosure provides a set of tagged nucleotides comprising at least two different polypeptide-tagged nucleotides each having a different polypeptide tag, wherein the at least two different polypeptide tags exhibit distinguishable blocking current levels and/or dwell times. In some embodiments of the set of tagged nucleotides, the at least two different polypeptide-tagged nucleotides comprise a compound of structure (I) or structure (II). In some embodiments, the at least two different polypeptide-tagged nucleotides each comprise a different polypeptide tag selected from Table 4. In some embodiments, the at least two different polypeptide tags exhibit blocking current levels that differ by at least 10%, at least 25%, at least 50%, or at least 75%. The measurement of the difference between blocking current levels can be made using any suitable nanopore detection method. For example, the blocking currents of each of the at least two different polypeptide-tagged nucleotides each having a different polypeptide tag can be measured in a nanopore static capture experiment, as is generally described in the Examples herein.

Nanopore Devices

Nanopore devices and methods for making and using them in nanopore detection applications such as nanopore sequencing using tagged nucleotides are known in the art (See e.g., U.S. Pat. Nos. 7,005,264 B2; 7,846,738; 6,617, 113; 6,746,594; 6,673,615; 6,627,067; 6,464,842; 6,362, 002; 6,267,872; 6,015,714; 5,795,782; and U.S. Publication Nos. 2015/0119259, 2014/0134616, 2013/0264207, 2013/ 0244340, 2004/0121525, and 2003/0104428, each of which are hereby incorporated by reference in their entirety). Nanopore devices useful for measuring nanopore detection are also described in the Examples disclosed herein. Generally, the nanopore devices all comprise pore-forming protein embedded in a lipid-bilayer membrane, wherein the membrane is immobilized or attached to a solid substrate which comprises a well or reservoir. The pore of the nanopore extends through the membrane creating a fluidic connection between the cis and trans sides of the membrane. Typically, the solid substrate comprises a material selected from the group consisting of polymer, glass, silicon, and a combination thereof. Additionally, the solid substrate comprises adjacent to the nanopore, a sensor, a sensing circuit, or an electrode coupled to a sensing circuit, optionally, a complementary metal-oxide semiconductor (CMOS), or field effect transistor (FET) circuit. Typically, there are electrodes on the cis and trans sides of the membrane that allow for a DC or AC voltage potential to be set across the membrane which generates a baseline current flow (or Open Current level) through the pore of the nanopore. The presence of a tag, such as a polypeptide tag of the present disclosure results in blocking this current flow and thereby generating a blocking current level relative to the open current that can be measured.

It is contemplated that the polypeptide-tagged nucleotide compounds of the present disclosure can be used with a wide range nanopore devices comprising nanopores generated by both naturally-occurring, and non-naturally occurring (e.g., engineered or recombinant) pore-forming proteins. A wide range of pore-forming proteins are known in the art that can be used to generate nanopores useful for nanopore detection of the polypeptide-tagged nucleotides of the present disclosure. Representative pore forming proteins include, but are not limited to, α-hemolysin, β-hemolysin, γ-hemolysin, aerolysin, cytolysin, leukocidin, melittin, MspA porin and porin A. The pore-forming protein, α-hemolysin from *Staphyloccocus aureus* (also referred to herein as "α-HL"), is one of the most-studied members of the class of pore-forming proteins, and has been used extensively in creating nanopore devices. (See e.g., U.S. Publication Nos. 2015/ 0119259, 2014/0134616, 2013/0264207, and 2013/ 0244340) α-HL also has been sequenced, cloned, extensively characterized structurally and functionally using a wide range of techniques including site-directed mutagenesis and chemical labelling (see e.g., Valeva et al. (2001), and references cited therein). A heptameric complex of α-HL monomers spontaneously forms a nanopore that embeds in and creates a pore through a lipid bilayer membrane. It has been shown that heptamers of α-HL comprising a ratio of 6:1 native α-HL to mutant α-HL can form nanopores (see e.g., Valeva et al. (2001), and references cited therein). Further, α-HL has been engineered with cysteine residue substitutions inserted at numerous positions allowing for covalent modification of the protein through maleimide linker chemistry (Ibid.) For example, the engineered α-hemolysin-C46 ("α-HL-C46"), comprises a K460 amino acid residue substitution that allows for modification with a linker that can be used to covalently attach a strand-extending enzyme, such as polymerase, using common click reaction chemistry. Alternatively, the α-HL heptamer can be modified covalently with a DNA-polymerase using a Spy-Catcher/SpyTag conjugation method as described in the Examples.

Accordingly, in some embodiments, the tagged nucleotide compositions of the present disclosure can be used with a nanopore device, wherein the nanopore comprises a heptameric α-HL complex, which has 6:1 native α-HL to a modified, or engineered version of α-HL, wherein the modified α-HL is conjugated covalently to a strand-extending enzyme, such as DNA polymerase. For example, the engineered α-HL-C46 can be modified with a linker allowing the use of tetrazine-trans-cyclooctene click chemistry to covalently attach a Bst2.0 variant of DNA polymerase to the heptameric 6:1 nanopore. Such an embodiments is described in U.S. Provisional Application No. 62/130,326, filed Mar. 9, 2015, which is hereby incorporated by reference herein.

The polypeptide-tagged nucleotides and associated methods provided herein can be used with a wide range of strand-extending enzymes such as the polymerases and ligases are known in the art. Exemplary polymerases that may be used with the compounds and methods of the present disclosure include the nucleic acid polymerases such as DNA polymerase (e.g., enzyme of class EC 2.7.7.7), RNA polymerase (e.g., enzyme of class EC 2.7.7.6 or EC 2.7.7.48), reverse transcriptase (e.g., enzyme of class EC 2.7.7.49), and DNA ligase (e.g., enzyme of class EC 6.5.1.1). In some embodiments, the polymerase useful with polypeptide-tagged nucleotides is 9° N polymerase, E. coli DNA Polymerase I, Bacteriophage T4 DNA polymerase, Sequenase, Taq DNA polymerase, 9° N polymerase (exo-)A485L/Y409V or Phi29 DNA polymerase (φ29 DNA Polymerase). In some embodiments, the strand extending enzyme that incorporates the polypeptide-tagged nucleotides comprises a DNA polymerase from Bacillus stearothermophilus. In some embodiments, the large fragment of DNA polymerase from B. stearothermophilus. In one embodiment, the polymerase is DNA polymerase Bst 2.0 (commercially available from New England BioLabs, Inc., Massachusetts, USA). In one embodiment, the polymerase is Pol2 DNA polymerase-D44A.

EXAMPLES

Various features and embodiments of the disclosure are illustrated in the following representative examples, which are intended to be illustrative, and not limiting. Those skilled in the art will readily appreciate that the specific examples are only illustrative of the invention as described more fully in the claims which follow thereafter. Every embodiment and feature described in the application should be understood to be interchangeable and combinable with every embodiment contained within.

Example 1: Preparation of Polypeptide-Tagged Nucleotides

This example illustrates a general method for preparation of any polypeptide-tagged nucleotides of structural formula (I) or (II) using any of the polypeptide tags listed in Table 4, or any polypeptide tag that is modified with propargyl group or other alkyne moiety (e.g., with an N-terminal propargyl-glycine ("Pra") amino acid residue). This example specifically exemplifies the steps in the preparation of dT6P-Linker-(EAAA)$_{16}$-E$_5$, which corresponds to compound (1) shown below.

(1)

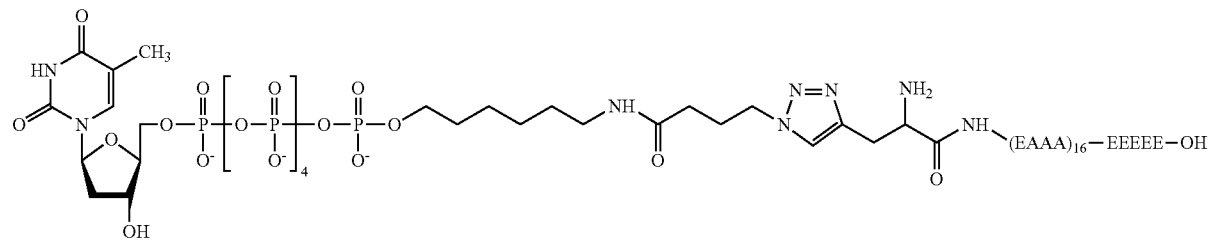

The polypeptide-tagged nucleotide of compound (1) was synthesized in an azido-alkyne click reaction between the 69-mer polypeptide tag, (EAAA)-E$_5$, which is modified with an N-terminal propargyl-glycine amino acid residue (e.g., as in the compound of structural formula (V)), and the azide-linker-modified nucleoside hexaphosphate, dT6P-N$_3$ shown as the compound (2):

(2)

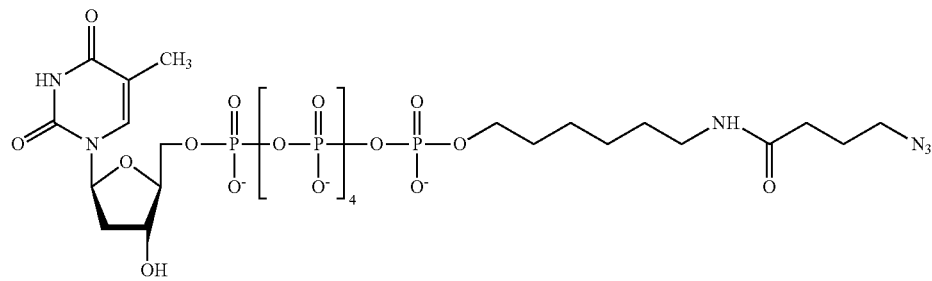

A. Synthesis dT6P-Azide (Compound (2))

The azide-linker-modified nucleoside hexaphosphate of compound (2) (dT6P-N$_3$) is prepared following the general reaction scheme depicted in FIG. 1. This general reaction scheme can be used for modifying any nucleoside-hexaphosphate compound, dN6P, with a hexylamine linker and an azide group. Briefly, 6-Fmoc-aminohexanol (1 g, 2.94 mmol) (1 in FIG. 1) is coevaporated with anhydrous acetonitrile (2×20 ml) and then dissolved in triethyl phosphate (10 ml). To this cooled and stirred solution is added fresh, distilled phosphorous oxychloride (550 µl, 5.88 mmol) and the mixture is stirred for 2 hr at 0° C. Tributylammonium pyrophosphate (5 eq., 15 mmol, 0.5 M solution in anhydrous DMF) and tributylamine (15 mmol) is added and this mixture stirred for 20 min. The solution is quenched with 0.1 M triethylammonium bicarbonate buffer (TEAB, 200 ml, pH7.5) and adjusted to pH~7. This solution is loaded on a Sephadex A-25 column and eluted using 0.1 M to 1.0 M TEAB buffer (pH 7.0) gradient. The appropriate fractions are collected, pooled, and further purified on reverse phase HPLC on Supelcosil™ LC-18-T (Supelco) 3 µM, 15 cm×4.6 mm. (HPLC parameters: Mobile phase: A, 8.6 mM Et$_3$N, 100 mM HFIP in water at pH 8.1; B, 100% methanol. Started from 100% A/0% B to 0% A/100% B in 40 minutes.) The pure triphosphate, $^{31}$P-NMR (D$_2$O) exhibits following shifts: δ: −7.68 (d, 1 P), −10.5 (d, 1 P), −22.65 (t, 1 P). The Fmoc-aminohexyltriphosphate produced (200 mg, 0.35 mmol) (2 in FIG. 1) is coevaporated with anhydrous acetonitrile (2×10 ml) and then dissolved in anhydrous DMF (3 ml). CU (4 eq., 1.4 mmol) is added and the solution stirred at room temperature for 4 h. Methanol (6 eq., 85 µl) is added with further stirring for 30 min. To the above product (3), a solution of the desired 2'-deoxynucleoside-5'-triphosphate (dNTP, tributylammonium salt, 0.5 mmol) in DMF and MgCl$_2$ (10 equivalents, 3.5 mmol) is added. This reaction mixture is stirred for 18 h followed by the addition of 10% triethylamine in water (25 ml) to hydrolyze the Fmoc group and yield the desired linker-modified nucleotide hexaphosphate compound, dN6P-NH$_2$ (4-7 in FIG. 1). The reaction mixture is stirred further for 16 h and the precipitated solid is filtered and the solution extracted with ether. The aqueous layer is concentrated and purified on reverse phase HPLC (Supelcosil™ LC-C18-T (Sulpelco) 3.0 µm particle size, 15 cm×4.6 mm) using the following parameters: 100% A/0% B in 4 min, then linear gradient change to 70% A/30% B for 30 minutes, and finally 0% A and 100% B for another 45 min at room temperature at a flow rate of 1 ml/min; mobile phase: A, 0.1 M TEAA; B, 100% ACN). The dN6P-NH$_2$ product can be characterized by $^{31}$P-NMR based on the following shifts: δ−10.63 (bs, 1P), −11.65 (bs, 1P), −23.35 (bm, 4P). MALDI-TOF MS for the four commonly used linker-modified dN6P compounds: dA6P-NH$_2$: 832.02 (calculated 829); dT6P-NH2: 825.97 (calculated 820); dG6P-NH2: 848.33 (calculated 845); dC6P-NH2: 826.08 (calculated 828.0).

The desired azide-modified compound dN6P-N$_3$ (8-11 in FIG. 1) is prepared by dissolving dN6P-NH$_2$ (10 µmol) in 0.1 M bicarbonate-carbonate buffer (500 µl, pH 8.7) and azidobutyric acid-NHS (25 µmol) in 200 µl DMF. This reaction mixture is stirred overnight then purified by HPLC using the same HPLC parameters and conditions described above for the dN6P-NH$_2$ compound. MALDI-TOF MS for the four commonly used azide-modified dN6P compounds: dA6P-N$_3$: 963.75 (calculated 963.3 as Na$^+$ salt); dT6P-N$_3$: 934.58 (calculated 932.3); dG6P-N$_3$: 960.27 (calculated 957.4); dC6P-N$_3$: 919.09 (calculated 917.4).

B. Synthesis of Propargyl-Modified Polypeptide Tag, Pra-(EAAA)-E$_5$

The N-terminal propargyl-glycine modified polypeptide tag, Pra-(EAAA)-E$_5$ was synthesized by means of fluorenylmethyloxycarbonyl (Fmoc) solid phase peptide synthesis on TentaGel® S PHB resin using an automated Multisyntech multiple peptide synthesizer. 4.0 equivalents of each of the amino acid derivatives used (i.e., Fmoc-Pra-OH, Fmoc-Ala-OH, Fmoc-Glu(OtBu)-OH) was dissolved in N-methylpyrrolidone containing 1 equivalent of 1-hydroxy-7-azabenzotriazol. Coupling reactions were carried out for 5 minutes in dimethylformamide (DMF) as a reaction medium with 4 equivalents HATU and 8 equivalents of N,N-diisopropylethylamine relative to resin loading. The Fmoc group was cleaved in 8 minutes after each synthesis step using 25% piperidine in DMF. Release of the polypeptide from the synthesis resin and the cleavage of the acid-labile protecting groups was achieved in 3 hours at room temperature with 9.5 mL trifluoroacetic acid, 0.25 mL triisopropylsilane, and 0.25 mL water. The reaction solution was subsequently mixed with cooled diisopropyl ether to precipitate the polypeptide.

The precipitate was filtered, washed again with diisopropyl ether, dissolved in a small amount of aqueous acetic acid or NaOH and lyophilized. The crude material obtained was purified by preparative RP-HPLC using a gradient of acetonitrile/water containing 0.1% trifluoroacetic acid. The identity of the purified propargyl-modified polypeptide tag, Pra-(EAAA)-E$_5$ was confirmed by means of ion spray mass spectrometry: ESI-MS$_{calc}$: M$^+$=6237.4; ESI-MS$_{exp}$: [M+4H]$^{4+}$=1559.7.

A variety of propargyl-modified polypeptide tags prepared using the synthesis method of this Example are shown in Table 5. The amino acid derivatives used for synthesizing the various polypeptide tags included: Fmoc-Pra-OH, Fmoc-Ala-OH, Fmoc Glu(OtBu)-OH, Fmoc-Pro-OH, Fmoc-Lys(Boc)-OH, Fmoc-β-Ala-OH and Fmoc-Gla(OtBu)$_2$-OH.

TABLE 5

(Seq. ID. Nos 15-24)

| Modified[1,2] Polypeptide Tag | MS Analysis | AA Sequence |
| --- | --- | --- |
| Pra-(EAAA)$_{16}$-E$_5$ | ESI-MS$_{CALC}$: M$^+$ = 6237.4<br>ESI-MS$_{EXP}$: [M + 4H]$^{4+}$ = 1559.7 | Pra*EAAAEAAAEAAAEAAAEAAAE<br>AAAEAAAEAAAEAAAEAAAEAAAE<br>AAAEAAAEAAAEAAAEAAAEEEEE |
| Pra-(EAAA)$_{13}$-E$_5$ | ESI-MS$_{CALC}$: M$^+$ = 5210.3<br>ESI-MS$_{EXP}$: [M + 3H]$^{3+}$ = 1737.2 | Pra*EAAAEAAAEAAAEAAAEAAAE<br>AAAEAAAEAAAEAAAEAAAEAAAE<br>AAAEAAAEEEEE |

TABLE 5-continued (Seq. ID. Nos 15-24)

| Modified[1,2] Polypeptide Tag | MS Analysis | AA Sequence |
|---|---|---|
| Pra-(EAAA)$_{10}$-E$_5$ | ESI-MS$_{CALC}$: M$^+$ = 4183.3<br>ESI-MS$_{EXP}$: [M + 3H]$^{3+}$ = 1395.3 | Pra*EAAAEAAAEAAAEAAAEAAAE<br>AAAEAAAEAAAEAAAEAAAEEEEE |
| Pra-(EAAA)$_8$-P-(EAAA)$_8$-E$_5$ | ESI-MS$_{CALC}$: M$^+$ = 6334.5<br>ESI-MS$_{EXP}$: [M + 4H]$^{4+}$ = 1584.3 | Pra*EAAAEAAAEAAAEAAAEAAAE<br>AAAEAAAEAAAPEAAAEAAAEAAA<br>EAAAEAAAEAAAEAAAEAAAEEEE<br>E |
| Biotin-(UE)$_{25}$-K(propargyl) | ESI-MS$_{CALC}$: M$^+$ = 5487.6<br>ESI-MS$_{EXP}$: [M + 4H]$^{4+}$ = 1372.5 | Biotin*UEUEUEUEUEUEUEUEUEU<br>EUEUEUEUEUEUEUEUEUEUEUE<br>UEUEUEUE*K(propargyl) |
| Pra-(EAAA)$_4$-P-(EAAA)$_4$-P(EAAA)$_4$-P(EAAA)$_4$-E$_5$ | ESI-MS$_{CALC}$: M$^+$ = 6528.7<br>ESI-MS$_{EXP}$: [M + 4H]$^{4+}$ = 1633.6 | Pra*EAAAEAAAEAAAEAAAPEAAA<br>EAAAEAAAEAAAPEAAAEAAAEAA<br>AEAAAPEAAAEAAAEAAAEAAAE<br>EEE |
| Pra-(EAAAKAAA)$_4$-(EAAA)$_8$-E$_5$ | ESI-MS$_{CALC}$: M$^+$ = 6233.6<br>ESI-MS$_{EXP}$: [M + 4H]$^{4+}$ = 1559.6 | Pra*EAAAKAAAEAAAKAAAEAAAK<br>AAAEAAAKAAAEAAAEAAAEAAAE<br>AAAEAAAEAAAEAAAEAAAEEEEE |
| Pra-(EAAAKAAA)$_8$-E$_5$ | ESI-MS$_{CALC}$: M$^+$ = 6229.9<br>ESI-MS$_{EXP}$: [M + 4H]$^{4+}$ = 1558.4 | Pra*EAAAKAAAEAAAKAAAEAAAK<br>AAAEAAAKAAAEAAAKAAAEAAAK<br>AAAEAAAKAAAEAAAKAAAEEEEE |
| Pra-(EPPP)$_{16}$-E$_5$ | ESI-MS$_{CALC}$: M$^+$ = 7487.1<br>ESI-MS$_{EXP}$: [M + 4H]$^{4+}$ = 1872.0 | Pra*EPPPEPPPEPPPEPPPEPPPE<br>PPPEPPPEPPPEPPPEPPPEPPPE<br>PPPEPPPEPPPEPPPEPPPEEEEE |
| Pra-(EAAA)$_{16}$-Gla$_4$-E | ESI-MS$_{CALC}$: M$^+$ = 6413.4<br>ESI-MS$_{EXP}$: [M + 4H]$^{4+}$ = 1604.6 | Pra*EAAAEAAAEAAAEAAAEAAAE<br>AAAEAAAEAAAEAAAEAAAEAAAE<br>AAAEAAAEAAAEAAAEAAA*Gla<br>GlaGla**Gla *E |

"Pra" = propargyl-glycine residue.
"U" = beta-alanine residue.
"Gla" = gamma-carboxy glutamic acid residue
"K(propargyl)" = a propargyl group covalently attached to the free epsilon amine on the side-chain of a C-terminal K residue. The propargyl group was introduced after cleavage of the polypeptide, Biotin-(UE)$_{25}$-K, from the synthesis resin, by reaction in liquid phase buffer (pH 7.5) with propargyl-N-hydroxysuccinimidester.

C. Click Reaction of dT6P-Azide and Pra-(EAAA)-E$_5$

The azido-alkyne click reaction to form the polypeptide-tagged nucleotide, dT6P-Linker-(EAAA)16-E5 of compound (1) can be carried out according to the same general scheme shown in the final step of FIG. 1, wherein the "TAG" attached to the desired dN6P-N$_3$ compound (8-11 in FIG. 1) is the polypeptide tag. The propargyl-glycine ("Pra") residue at the N-terminus of the polypeptide tag provides an alkyne group that undergoes the click reaction with the azide group on the nucleotide to form the covalent bond (via formation of a triazole moiety) that links a nucleotide dN6P to the N-terminal propargyl group of the modified polypeptide tag, Pra-(EAAA)$_{16}$-E$_5$.

Briefly, an aqueous solution (0.7 mL) Pra-polypeptide tag, Pra-(EAAA)-E$_5$ (400 nmol), dT6P-azide (1200 nmol), premixed CuSO$_4$/THPTA (6 µmol/30 µmop and Na-ascorbate (8 µmol) was shaken at 40° C. overnight. EDTA was added and the mixture was desalted by dialysis. The click-reaction product, dT6P-Linker-(EAAA)-E$_5$, was purified by preparative RP-HPLC with a triethylammonium acetate/acetonitrile gradient. The fractions containing pure conjugate were pooled and dried down by centrifugal vacuum concentration to give white solid. The formation of the polypeptide-tagged nucleotide, dT6P-Linker-(EAAA)-E$_5$ was confirmed by ion spray mass spectrometry: ESI-MS$_{calc}$: m/z=7168.8; ESI-MS$_{exp}$: m/z=7169.2.

Click reactions to form polypeptide-tagged dT6P according to the above-described method were also carried out using the following propargyl-modified polypeptide tags: Pra-(EAAA)$_{13}$-E$_5$, Pra-(EAAA)$_{10}$-E$_5$, and Pra-(EAAA)$_8$-P-(EAAA)$_8$-E$_5$. The formation of the expected polypeptide-tagged nucleotide compounds of formula (II) for each of these reactions was confirmed by ion spray mass spectrometry analysis as shown below:

Results of reaction of dT6P-azide+Pra-(EAAA)$_{13}$-E$_5$: ESI-MS$_{calc}$: m/z=6141.7; ESI-MS$_{exp}$: m/z=6141.7.

Results of reaction of dT6P-azide+Pra-(EAAA)$_{10}$-E$_5$: ESI-MS$_{calc}$: m/z=5114.7; ESI-MS$_{exp}$: m/z=5115.1.

Results of reaction of dT6P-azide+Pra-(EAAA)$_8$-P-(EAAA)$_8$-E$_5$: ESI-MS$_{calc}$: m/z=7265.9; ESI-MS$_{exp}$: m/z=7267.1.

Example 2: Nanopore Detection of Polypeptide-Tagged Nucleotide

This example illustrates the detection and measurement of the blocking current and dwell time characteristics of the polypeptide tagged nucleotide, dT6P-Linker-(EAAA)$_{16}$-E$_5$ (compound (1)) prepared in Example 1 using a "static capture" experiment with a nanopore array microchip detection system. In the "static capture" experiment, a complementary polypeptide-tagged nucleotide forms an active site ternary complex with a polymerase conjugated proximal to the nanopore but is not incorporated by the polymerase due to the absence of the required catalytic $Mg^{2+}$ cation. The polypeptide tag, however, is able to enter and reside in the pore of the nanopore. Since the electrodes of the nanopore system are under either a DC or AC potential, the presence of the tag in the nanopore creates a detectable blocking current.

Nanopore detection system: The nanopore blocking current measurements are performed using nanopore array microchip comprising a ~1×1 mm CMOS microchip that has an array of 264 silver electrodes (5 μm diameter) within shallow wells (chip fabricated by Genia Technologies, Mountain View, Calif., USA). Methods for fabricating and using such nanopore array microchips can also be found in U.S. Patent Application Publication Nos. 2013/0244340 A1, US 2013/0264207 A1, and US2014/0134616 A1 each of which is hereby incorporated by reference herein. Each well in the array is manufactured using a standard CMOS process with surface modifications that allow for constant contact with biological reagents and conductive salts. Each well can support a phospholipid bilayer membrane with a nanopore-polymerase conjugate embedded therein. The electrode at each well is individually addressable by computer interface. All reagents used are introduced into a simple flow cell above the array microchip using a computer-controlled syringe pump. The chip supports analog to digital conversion and reports electrical measurements from all electrodes independently at a rate of over 1000 points per second. Nanopore blocking current measurements can be made asynchronously at each of 264 addressable nanopore-containing membranes in the array at least once every millisecond (msec) and recorded on the interfaced computer.

Formation of lipid bilayer on chip: The phospholipid bilayer membrane on the chip is prepared using 1,2-diphytanoyl-sn-glycero-3-phosphocholine (Avanti Polar Lipids). The lipid powder is dissolved in decane at 15 mM and then painted in a layer across the 264 wells on the chip. A thinning process then is initiated by pumping air through the cis side of the array wells, thus reducing multi-lamellar lipid membranes to a single bilayer. Bilayer formation is tested using a ramping voltage from 0 to 1000 mV. A typical single bilayer would temporarily open at an applied voltage of between 300 to 500 mV.

Preparation of nanopore-polymerase conjugate: Two fragments of the collagen adhesion domain (CnaB2) of the *Streptococcus pyogenes* fibronectin-binding protein FbaB can specifically bind to each other and generate a peptide bond between the □-amino group of a lysine in one fragment (i.e., the "SpyCatcher") and the carboxyl side group of an aspartic acid in the other fragment (i.e., the "SpyTag"). In the present example, the SpyTag fragment is attached via a short peptide linker to the N-terminus of α-HL monomer having an H144A mutation, and the SpyCatcher fragment is attached via a similar short peptide linker to the N-terminus of the Pol2 DNA polymerase having a D44A mutation. α-HL monomers with and without the SpyTag were mixed allowing assembly of heptameric nanopores, and those heptameric nanopores with only one SpyTag-modified α-HL monomer were purified by chromatography to provide the desired 6:1 α-HL nanopores. The 6:1 α-HL nanopore solution was then combined with the SpyCatcher-modified Pol2 DNA polymerase-D44A to form the 6:1 α-HL-Pol2 conjugates.

Nanopore-polymerase conjugate insertion in membrane: After the lipid bilayer formed on the 256 wells of the chip, 3 μM of the polypeptide-tagged nucleotide of compound (1), 0.1 μM of a 6:1 α-HL-Pol2 nanopore-polymerase conjugate, 0.4 μM of the desired "JAM1A" DNA template, all in a buffer solution of 3 mM $CaCl_2$), 20 mM Hepes, and 300 mM NaCl, pH 7.5 (for DC mode) or 500 mM potassium glutamate, pH8 (for AC mode), at 20° C. was added to the cis side of the chip. The nanopore-polymerase conjugate in the mixture spontaneously inserts into the lipid bilayer. Since only Ca' and no Mg' metal ion was present, the ternary complex at the DNA polymerase was able to form at the active site but the nucleotide was not incorporated and the 5'-phosphate-linked tag was not released.

The "JAM1A" DNA template is a 99-mer self-priming single-strand. This DNA templates has a first available position on the template for binding to the complementary dT nucleotide.

Nanopore blocking current measurements: The same buffer solution used for inserting nanopore conjugate and DNA template (300 mM NaCl, pH 7.5 (for DC mode) or 500 mM potassium glutamate, pH 8 (for AC mode), 3 mM $CaCl_2$), 20 mM Hepes, at 20° C.) was also used as the electrolyte solution for the nanopore current blockade measurements. For DC mode, a 100 mV (cis vs. trans) voltage was applied across the chip-board between two Ag/AgCl electrodes placed on either side of the membrane and pore. For AC mode, a Pt/Ag/AgCl electrode setup was used and a −10 mV to 200 mV square waveform was applied.

Figure 2:
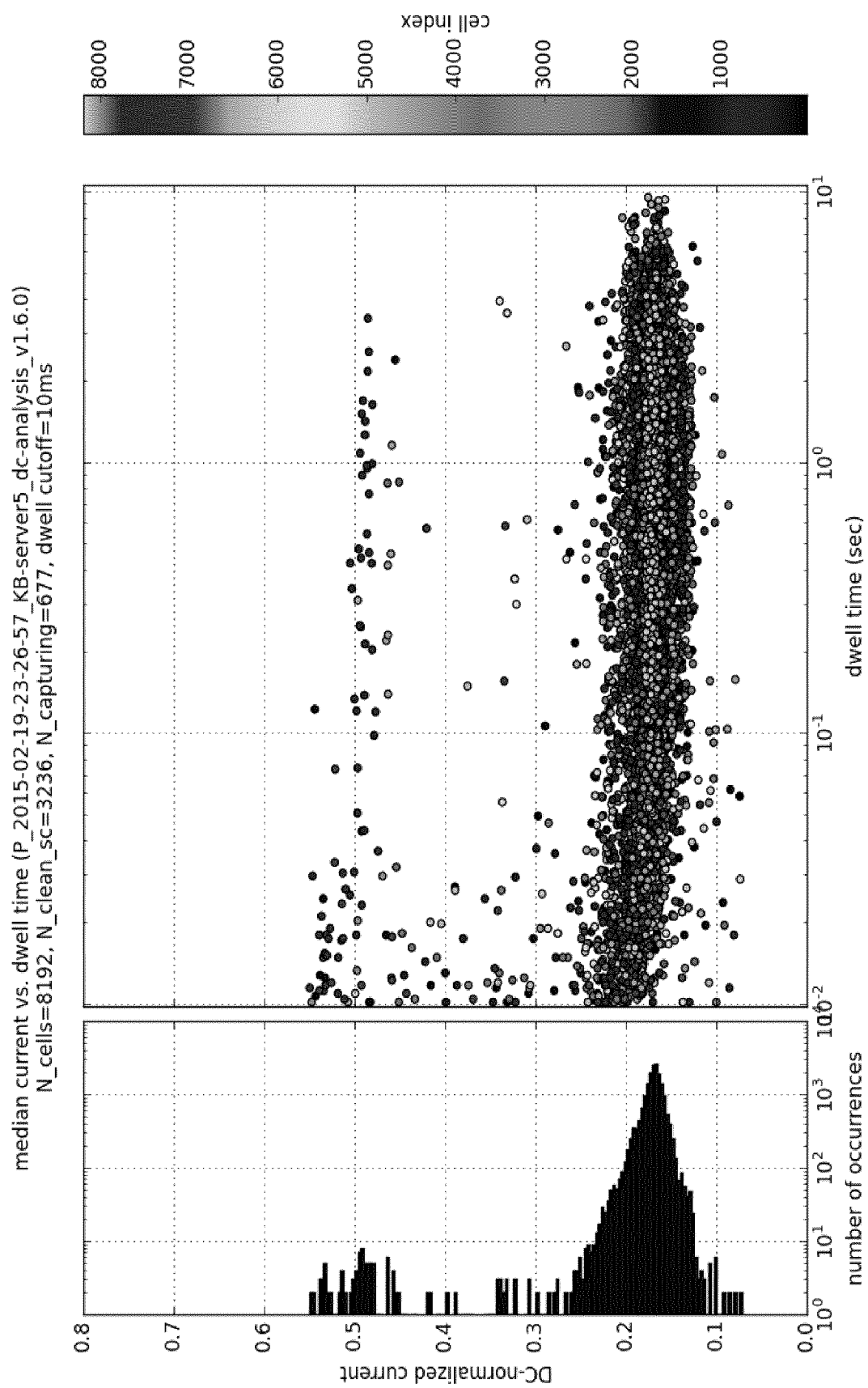
FIG. 2 depicts "static capture" nanopore detection data for the polypeptide-tagged nucleotide dT6P-Linker-(EAAA)$_{16}$-E$_5$ using an α-HL-Pol2 polymerase conjugate, complexed with a JAM1A DNA template, and embedded in a membrane under a 100 mV DC potential. As described in Example 2, the dT6P-Linker-(EAAA)$_{16}$-E$_5$ exhibits a strong blocking current of 20% O.C. (with low variance) and a long mean dwell time of ~975 ms.

FIG. 2 shows results for a static capture experiment carried out in DC mode. Numerous current blockade events were plotted for the polypeptide-tagged nucleotide with the application of voltage across the pore. FIG. 2 shows plots based on two detectable characteristics of the blocking current events: (1) blocking current as a percentage of the background current or "open current" of the pore ("O.C."), and (2) average dwell time in milliseconds. A histogram of current blockade event dwell times observed for each different tagged nucleotide was fit to the exponential function $y=A\,e^{-Bx}$ and the reciprocal of constant B used as the calculated average dwell time. Current blocking events with average dwell times longer than 10 ms and a blocking current below 60% of open current were deemed to be indicative of productive capture of the tagged nucleotide by the polymerase conjugated to the nanopore (i.e., binding of the tagged nucleotide with the complementary template base at the polymerase active site and the "tail" of the tagged nucleotide positioned in the adjacent pore).

Results: The polypeptide-tagged nucleotide, dT6P-Linker-$(EAAA)_{16}$-$E_5$ of compound (1) exhibited a consistently high blocking current of 17% of open current with a low variance of 1.7%. The mean dwell time was 975 ms, which is significantly longer than dwell times observed for other types of tags used in nanopore detection experiments, such as 30-mer oligonucleotides, which exhibit mean dwell times in the range of 15-30 ms.

Example 3: Nanopore Capture of Different Polypeptide-Tagged Nucleotides Under Alternating Current (AC) Conditions This example illustrates the measurement and comparison of the blocking current characteristics four polypeptide-tagged nucleotides under nanopore detection "static capture" using AC voltage, and compares the blocking currents of three polypeptide-tagged nucleotides with helical structure and varying overall charge, dT6P-Linker-$(EAAA)_{16}$-$E_5$, dT6P-Linker-$(EAAA)_{13}$-$E_5$, and dT6P-Linker-$(EAAA)_8$-P-$(EAAA)_8$-$E_5$, the blocking current of a polypeptide-tagged nucleotide, dT6P-Linker-(UE)$_{25}$-biotin, which has predominantly random coil structure.

The two polypeptide-tagged nucleotides are prepared via click reactions between dT6P-N$_3$ and the corresponding propargyl-modified polypeptide tags, Pra-(EAAA)$_{16}$-E$_5$ and (propargyl)K(UE)$_{25}$-biotin, according to the methods described in Example 1. The nanopore detection system is the 264 nanopore array microchip with the nanopore-polymerase conjugate inserted in the membrane complexed with the JAM1A DNA template as described in Example 2. The nanopore well solution is 500 mM potassium glutamate (KGlu), 3 mM CaCl$_2$), 20 mM HEPES, pH 8, and rather than a 100 mV DC voltage, an AC voltage of 210 mV peak-to-peak is run across the membrane electrodes.

As noted elsewhere herein, an AC current can have certain advantages for nanopore detection as it allows for the polypeptide tag to be repeatedly directed into and then expelled from the nanopore thereby providing more opportunities to detect the tag. AC current also can provide a steadier potential for a more stable current signal and less degradation of the electrodes over time.

Figure 3:
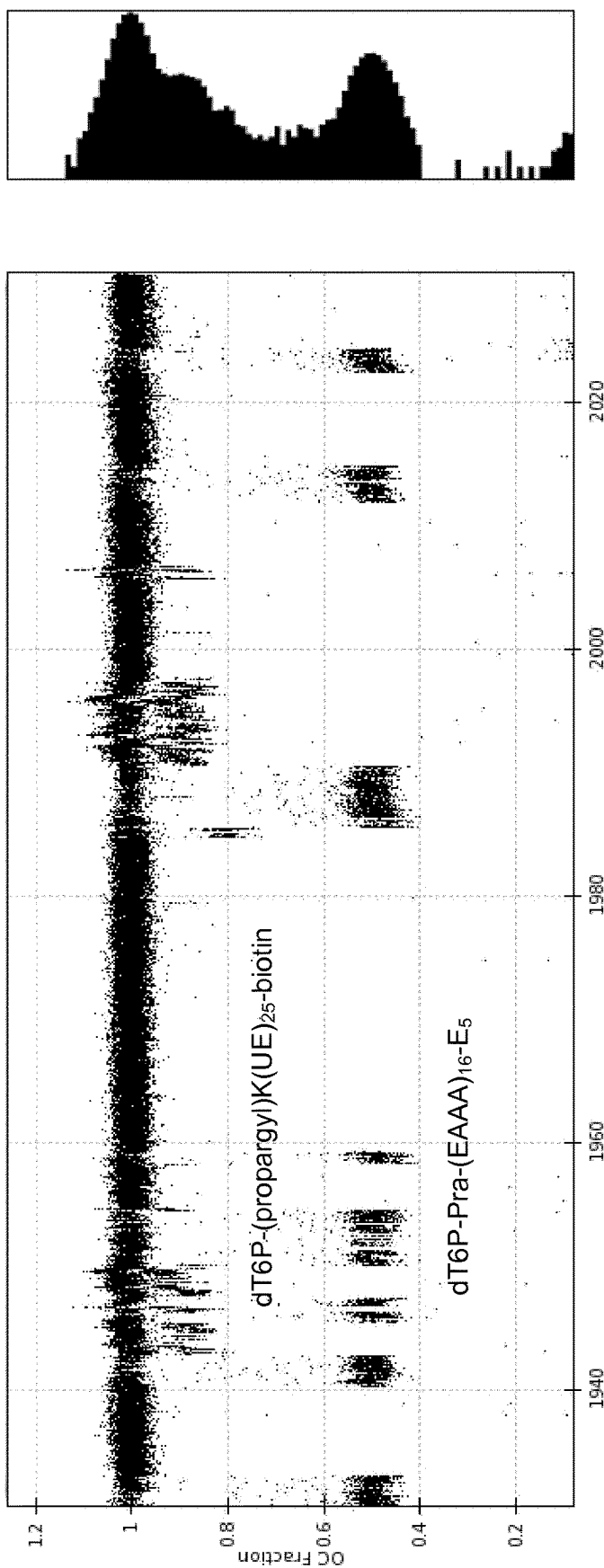
FIG. 3 depicts "static capture" nanopore detection data for two different polypeptide-tagged nucleotides, dT6P-Linker-(EAAA)$_{16}$-E$_5$ and dT6P-(propargyl)K(UE)$_{25}$-biotin. Nanopore detection is with an α-HL-Pol2 polymerase conjugate, complexed with a JAM1A DNA template, and embedded in a membrane under a 250 mV (peak-to-peak) AC potential. As described in Example 3, the dT6P-Linker-(EAAA)$_{16}$-E$_5$ (which has helical structure) and dT6P-(propargyl)K(UE)$_{25}$-biotin (which has only random coil structure) exhibit easily distinguishable blocking currents of 50% O.C. and 80-90% O.C.

A 3 μM solution of first dT6P-Linker-(EAAA)$_{16}$-E$_5$ and then dT6P-Linker-(UE)$_{25}$-biotin is added to the cis side of the chip and the distinctly different blocking currents for the capture events for the two polypeptide-tagged nucleotides are measured and plotted versus time. A resulting plot is shown in FIG. 3. Nanopore capture of dT6P-Linker-(EAAA)$_{16}$-E$_5$ results in a much higher blocking current of about 50% O.C., whereas nanopore capture of dT6P-Linker-(UE)$_{25}$-biotin results a significantly lower blocking current of about 80-90% O.C. (NOTE: a lower percentage of open current indicates higher blocking of the open current, therefore a higher blocking current.) Thus, polypeptide-tagged nucleotides with two different polypeptide tags are capable of providing highly distinguishable blocking currents under nanopore array detection conditions useful for nucleic acid sequencing.

Additionally, nanopore static capture measurements are carried out on the wo other polypeptide-tagged nucleotides with helical structure, dT6P-Linker-(EAAA)$_{13}$-E$_5$ and dT6P-Linker-(EAAA)$_8$-P-(EAAA)$_8$-E$_5$ yield similar results. Both exhibit high blocking currents of 50-55% O.C. similar to the blocking current of dT6P-Linker-(EAAA)$_{16}$-E$_5$ which has similar helical structure.

The invention claimed is:

1. A method for determining the sequence of a nucleic acid comprising:
   (a) providing a nanopore sequencing composition comprising: a membrane, an electrode on the cis side and the trans side of the membrane, a nanopore with its pore extending through the membrane, an electrolyte solution in contact with both electrodes, an active polymerase situated adjacent to the nanopore, and a primer strand complexed with the polymerase;
   (b) contacting the nanopore sequencing composition with (i) a strand of the nucleic acid; and (ii) a set of tagged nucleotides each with a different tag, wherein each different tag causes a different blocking current and/or blocking voltage and/or has a different dwell time when it is situated in the nanopore, and the set comprises at least one compound of structural formula (I):

N-P-L-T    (I)

wherein,
   N is a nucleoside;
   P is an oligophosphate covalently attached to a 5'-O group of the nucleoside, wherein the oligophosphate consists of 3 to 12 phosphate groups;
   L is a linker covalently attached to a terminal phosphate group of the oligophosphate; and
   T is a polypeptide tag covalently attached to the linker, wherein the polypeptide has an overall charge and comprises at least one helical structure, wherein the helical structure is an α-helix comprising the sequence motif (EAAA)16-E5; and (c) detecting the different blocking currents and/or blocking voltages and/or different dwell times of the tags over time and correlating to each of the different tagged nucleotides incorporated by the polymerase which are complimentary to the nucleic acid sequence, and thereby determining the nucleic acid sequence.

2. The method of claim 1, wherein the compound comprises structural formula (II):

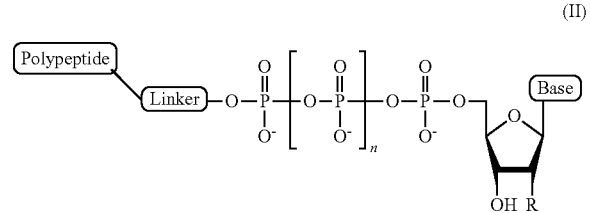

(II)

Base is selected from the group consisting of adenosine, cytidine, guanosine, thymidine, and uridine;
R is selected from the group consisting of H and OH;
n is from 1 to 4;
Linker is a linker comprising a covalently bonded chain of 2 to 100 atoms; and
Polypeptide is a polypeptide tag comprising an overall charge and at least one helical structure.

3. The method of claim 1, wherein the length of the polypeptide tag is at least 16 amino acid residues.

4. The method of claim 1, wherein the length of the polypeptide tag is at least 20 amino acid residues.

5. The method of claim 1, wherein the length of the polypeptide tag is at least 25 amino acid residues.

6. The method of claim 1, wherein the length of the polypeptide tag is at least 30 amino acid residues.

7. The method of claim 1, wherein the length of the polypeptide tag is at least 40 amino acid residues.

8. The method of claim 1, wherein the helical structure comprises at least 8 amino acid residues.

9. The method of claim 1, wherein the helical structure comprises at least 16 amino acid residues.

10. The method of claim 1, wherein the helical structure comprises at least 20 amino acid residues.

11. The method of claim 1, wherein the overall charge of the polypeptide tag is negative, optionally wherein the overall charge of the polypeptide tag is between about −10 and −30.

12. The method of claim 1, wherein the 25% of the amino acid residues located at the end of the polypeptide tag distal from the linker have a net charge absolute value greater than the net charge absolute value of the 25% of the amino acid residues located at the end of the polypeptide tag proximal to the linker.

13. The method of claim 1, wherein P consists of from 3 to 9 phosphate groups.

14. The method of claim 1, wherein P consists of from 4 to 6 phosphate groups.

15. The method of claim 1, wherein P consists of 6 phosphate groups.

16. The method of claim 1, wherein the linker comprises a chemical group selected from the group consisting of: ester, ether, thioether, amine, amide, imide, carbonate, carbamate, squarate, thiazole, thiazolidine, hydrazone, oxime, triazole, dihydropyridazine, phosphodiester, polyethylene glycol (PEG), and combinations thereof.

* * * * *